United States Patent
Jakóczi et al.

[11] Patent Number: 6,130,215
[45] Date of Patent: Oct. 10, 2000

[54] PIPERAZINYLALKYLTHIOPYRIMIDINE DERIVATIVES, PHARMACEUTICAL COMPOSITIONS CONTAINING THE SAME AND A PROCESS FOR THE PREPARATION OF THE NOVEL COMPOUNDS

[75] Inventors: Iván Jakóczi, Monor; Dániel Bózsing, Budapest; Ildikó Rátz née Simonek, Budapest; István Gacsályi, Budapest; Gábor Szénási, Budapest; Éva Schmidt, Budapest; Anikó Miklós née Kovács, Budapest; András Bilkei-Gorzó, Budapest; Gábor Blaskó, Budapest; István Gyertyán, Budapest; Gábor Németh, Budapest; Gyula Simig, Budapest; Károly Tihanyi, Budapest; András Egyed, Budapest, all of Hungary

[73] Assignee: Egis Gyóyszergyár RT, Budapest, Hungary

[21] Appl. No.: 09/066,465

[22] PCT Filed: Oct. 25, 1996

[86] PCT No.: PCT/HU96/00061

§ 371 Date: Jun. 23, 1998

§ 102(e) Date: Jun. 23, 1998

[87] PCT Pub. No.: WO97/16429

PCT Pub. Date: May 9, 1997

[30] Foreign Application Priority Data

Oct. 31, 1995 [HU] Hungary ................... 9503099

[51] Int. Cl.[7] .................................................. A01N 43/58
[52] U.S. Cl. ................... 514/252; 544/295; 540/575; 514/212
[58] Field of Search .................... 544/295; 514/252

[56] References Cited

FOREIGN PATENT DOCUMENTS 0202654 11/1986 European Pat. Off. .

OTHER PUBLICATIONS

Sleight et al., "The Clinical Utility of Serotonin Receptor Active Agents in Neuropsychiatric Disease," Serotonin Receptor Subtypes: Basic and Clinical Aspects, pp. 211–227 (1991) Wiley–Liss, Inc.

Database CAPLUS on STN, Chemical Abstract, vol. 129, No. 310332, Balogh et al., "A new validated high–performance liquid chromatographic method for the determination of EGIS–9933 in rat plasma," abstract, Chromatographia, vol. 48, No. 1/2, pp. 158–162, 1998.

*Primary Examiner*—Mukund J. Shah
*Assistant Examiner*—Ann M. Kessinger
*Attorney, Agent, or Firm*—Birch, Stewart, Kolasch & Birch, L.L.P.

[57] ABSTRACT

The invention refers to novel piperazinylalkylthiopyrimidine derivatives of formula (I) being suitable for the treatment of diseases due to pathological alterations of the central nervous system, pharmaceutical compositions containing the above derivatives, and a process for the preparation of the novel compounds.

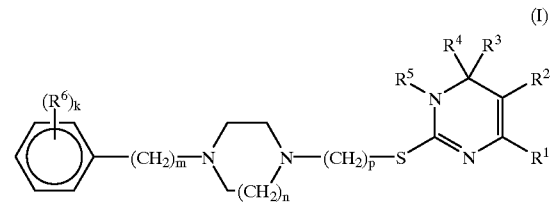

4 Claims, No Drawings

PIPERAZINYLALKYLTHIOPYRIMIDINE DERIVATIVES, PHARMACEUTICAL COMPOSITIONS CONTAINING THE SAME AND A PROCESS FOR THE PREPARATION OF THE NOVEL COMPOUNDS

This application claims the benefit under 35 U.S.C. §371 of prior PCT International Application No. PCT/HU96/00061, which has an International filing date of Oct. 25, 1996, which designated the United States of America, the entire contents of which are hereby incorporated by references.

The invention refers to novel piperazinylalkylthiopyrimidine derivatives, pharmaceutical compositions containing the above derivatives, a method for the treatment of diseases of especially the central nervous system, and a process for the preparation of the novel compounds.

Specifically, the invention refers to compounds of the formula

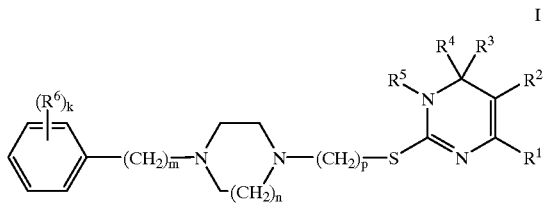

I wherein
- $R^1$ and $R^3$ represent, independently, a hydrogen, a $C_{1-4}$ alkyl group, an amino group, a $(C_{1-4}$ alkanoyl) amino group, or a phenyl group optionally bearing 1 to 3 substituents selected from the group consisting of, independently, a halo, a $C_{1-4}$ alkoxy group, a di($C_{1-4}$ alkyl)amino group or a benzyloxy group,
- $R^2$ stands for a hydrogen, a cyano group, a furylmethyl group, a $(C_{5-7}$ cycloalkyl)methyl group, a $(C_{1-4}$ alkoxy) carbonyl group, a hydroxy($C_{1-4}$ alkyl) group or a benzyl group optionally bearing 1 to 3 substituents selected from the group consisting of, independently, a halo, a $C_{1-4}$ alkyl group, a $C_{1-4}$ alkoxy group, a trifluoro methyl group, a hydroxy group, a benzyloxy group or a di($C_{1-4}$ alkyl)amino group,
- $R^4$ means hydrogen, or
- $R^3$ forms with $R^4$ an oxygen atom,
- $R^5$ is hydrogen, or
- $R^4$ forms with $R^5$ a valence bond,
- $R^6$ represents a halo, a cyano group, a nitro group, a $C_{1-4}$ alkyl group, a $C_{1-4}$ alkoxy group or a trifluoromethyl group,
- m has a value of 0 or 1,
- n has a value of 1 or 2,
- p is an integer between 2 to 11, and
- k has a value of 0, 1, 2 or 3, and pharmaceutically acceptable acid addition salts thereof.

The novel piperazinylalkylthiopyrimidine derivatives can be employed, in the first place, for the treatment of diseases due to pathological alterations of the central nervous system.

Pyrimidine derivatives connected with a piperazine ring and used for the treatment of urination disorders are described by Japanese Patent Application No. J 3 090 027. Uracil compounds of similar type are known from DE-P No. 1 942 405. One of the known uracil compounds is urapidil, a blood pressure lowering drug. However, in case of the above compounds, the two heterorings are connected through an alkylamino group.

Pyrimidine derivatives bonded to a piperazine ring through an alkoxy group and having sedative and hypotensive activity are described by BE-P Nr. 756 127.

It was found that the novel compounds of the formula I, wherein the heterorings containing nitrogen atoms are connected through an alkylthio group, have excellent biological activity influencing the serotonerg system.

In the description, a $C_{1-4}$ alkyl group is a methyl, ethyl, n-propyl, isopropyl, sec.-butyl, tert.-butyl, n-butyl or isobutyl group. Preferably, $C_{1-4}$ alkyl is methyl.

A $C_{1-4}$ alkanoyl group is a formyl, acetyl, n-propanoyl, n-butanoyl etc. group, preferably an acetyl group.

In general, a halo is a fluoro, chloro or bromo, preferably chloro or bromo.

A $C_{1-4}$ alkoxy group is generally a methoxy, ethoxy, n-propoxy or n-butoxy group, preferably a methoxy group.

The pharmaceutically acceptable acid addition salts of the compounds of the formula I are acid addition salts of the compounds formed with pharmaceutically acceptable, inorganic or organic acids. Preferred acid addition salts are hydrogen haloids such as hydrochlorides or hydrobromides, carbonates, hydrogen carbonates, sulfates, phosphates, acetates, fumarates, maleates, citrates and ascorbates.

A preferred sub-group of the compounds of the invention consists of the compounds of the formula I, wherein
- $R^1$ and $R^3$ represent, independently, a hydrogen, a methyl group, an amino group, an acetylatnino group or a phenyl group optionally bearing 1 to 3 substituents selected from the group consisting of, independently, a chloro group, a methoxy group, a dimethylamino group or a benzyloxy group,
- $R^2$ stands for a hydrogen, a cyano group, a furylmethyl group, a cyclohexylmethyl group, an ethoxycarbonyl group, a hydroxyethyl group or a benzyl group optionally bearing 1 to 3 substituents selected from the group consisting of, independently, a chloro, a fluoro, a $C_{1-3}$ alkyl group, a methoxy group, a trifluoromethyl croup, a hydroxy group, a benzyloxy group or a dimethylamino group,
- $R^4$ means a hydrogen, or
- $R^3$ forms with $R^4$ an oxygen atom,
- $R^5$ is a hydrogen, or
- $R^4$ forms with $R^5$ a valence bond,
- $R^6$ represents a chloro, a fluoro, a cyano group, a nitro group, a methyl group, a methoxy group or a trifluoro methyl group,
- m has a value of 0 or 1,
- n has a value of 1 or 2,
- p has a value of 2 or 11, and
- k has a value of 0, 1, 2 or 3, and pharmaceutically acceptable acid addition salts thereof.

A specifically preferred sub-group of the compounds of the invention consists of the compounds of the formula I, wherein $R^1$ and $R^3$ represent an amino group,
- $R^2$ stands for a hydrogen or a benzyl group optionally bearing 1 to 3 substituents selected from the group consisting of, independently, a fluoro, a chloro, a methoxy group and a dimethylamino group,
- $R^4$ forms with $R^5$ a valence bond,
- $R^6$ means a fluoro, a chloro, a nitro group, a cyano group, a methyl group, a methoxy group or a trifluoromethyl group,
- k has a value of 1, m has a value of 1, n has a value of 1, and p has a-value of 2, and pharmaceutically acceptable acid addition salts thereof.

The piperazinylalkylthiopyrimidine derivatives of the invention are prepared by reacting a 2-mercaptopyrimidine of the formula

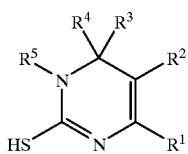

II wherein $R^1$, $R^2$, $R^3$, $R^4$ and $R^5$ are as defined above, or an alkali metal salt thereof with a haloalkylpiperazine derivative of the formula

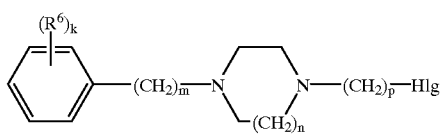

III wherein $R^6$, m, n, p and k are as stated above, Hlg stands for chloro or bromo, or an acid addition salt thereof, and, if desired, transforming an obtained compound of the formula I into a pharmaceutically acceptable acid addition salt or liberating the base from the acid addition salt.

The process of the invention is performed in a solvent or solvent mixture that is indifferent from the point of view of the reactants. For example aliphatic alcohols such as methanol, ethanol, isopropanol; dialkylamides preferably dimethylformamide; dialkyl sulfoxides preferably dimethyl sulfoxide; or the mixtures thereof can be used. It is especially preferred to react the reactants in methanol, dimethylformamide or a mixture of methanol and dimethylformamide.

The reaction of the 2-mercaptopyrimidine of the formula II with haloalkylpiperazine derivative of the formula III can be performed in the presence of an acid binding agent. Preferred acid binding agents are alkali metal carbonates such as sodium carbonate, alkali metal hydrocarbonates such as sodium or potassium hydrocarbonate, alkali metal hydroxides such as sodium or potassium hydroxide, alkali earth metal hydroxides such as calcium hydroxide or tertiary amines such as pyridine, triethylamine or other trialkylamines. Preferably, potassium carbonate or sodium carbonate is employed as the acid binding agent.

Optionally, a catalyst is used to accelerate the reaction. In general, alkali metal halides or alkali earth metal halides such as potassium iodide, potassium fluoride, sodium bromide or calcium chloride are employed as the catalyst. The reaction is preferably performed in the presence of potassium iodide catalyst.

Depending on the reactivity of the starting compounds, the reaction proceeds at a temperature between room temperature and the boiling point of the reaction mixture. It is preferred to react the reactants at 60 to 80° C.

The reaction time is 1 to 10 hours depending on the reactivity of the reactants and the reaction temperature used.

The starting compounds of the formulae II and III can be employed in an equimolar amount, or the haloalkylpiperazine derivative of the formula III is used up to 10 per cent excess, at the most. The acid binding agent is used in an equimolar quantity referring to the amount of the haloalkylpiperazine derivative of the formula III.

The catalyst is employed in 0.1 to 0.2 molar, preferably in 0.1 molar quantity for each mole of the starting compounds.

The reaction mixture is worked up in a manner known per se. Preferably, the product is separated as follows: the inorganic salts precipitated are filtered, the filtrate is distilled off in vacuo, and the residue is dissolved in water or an organic solvent to crystallize the product; or the product separated is filtered together with the inorganic salts, then the inorganic salts are removed by dissolution in water. A further alternative is to pour the reaction mixture into water in order to dissolve the inorganic salts, and filtering the product precipitated.

If desired, the reaction product is purified by known purification methods such as recrystallization or chromatography.

The compounds of the formula I can be also separated in the form of pharmaceutically acceptable acid addition salts mentioned above, or a compound of the formula I obtained as a base can be converted to acid addition salt in a subsequent step by reaction with the suitable acid in an indifferent solvent. From the acid addition salt, the base can be repeatedly liberated and optionally converted to another acid addition salt.

A large part of the starting compounds of the formula II is known from the literature or is commercially available. These known compounds can be prepared by the modified Traube's synthesis /W. Traube, Ann., 331, 64 (1904)/or by the method of José et al./Heterocycles, 19 (2), 305–311 (1982)/. However, the compounds of the formula II, wherein $R^1$ is an amino group, $R^2$ represents a nitrile group, $R^3$ stands for a 4-bromophenyl, 2- or 4-chlorophenyl, 2- or 4-methoxyphenyl, 4-dimethylaminophenyl, 4-benzyloxy-3-methoxyphenyl or 3,4,5-trimethoxyphenyl group, $R^4$ and $R^5$ mean hydrogen, as well as the compounds of the formula II, wherein $R^1$ and $R^3$ stand for an amino group, $R^2$ is a 2-furylmethyl, cyclohexylmethyl, benzyl or mono-, di- or trisubstituted benzyl group, $R^4$ forms together with $R^5$ a valence bond, are novel, that are not described in the literature. They can be prepared by the synthesis methods of the known compounds (e.g. European Patent Application No. 465 323).

A part of the haloalkylpiperazine derivatives of the formula III is also known from the literature. They can be prepared by means of the method described by e.g. C. B. Pollard et al./J. Org. Chem., 24, 764–767 (1959)/ or Sidney D. Ross et al./J. Am. Chem. Soc., 85 (24), 3999–4003 (1963)/. The starting compounds of the formula III, wherein $R^6$ represents a 2-nitro, 3-chloro, 3-nitrile, 3-trifluoromethyl, 4-methoxy or 4-methyl group, m has a value of 1, n has a value of 1 or 2, p has a value of 2, and Hlg is chloro or bromo, or $R^6$ stands for a 2,6-dinitro-4-trifluoromethyl or 2-nitro-4-trifluoromethyl group, m has a value of 0, n has a value of 1 or 2, p has a value of 2, and Hlg is a chloro or bromo, are novel compounds that can be prepared by the methods given in connection with the known compounds.

Compounds of the formula I have valuable biological activity.

Our studies revealed that the compounds of the invention bind strongly to different serotonin receptor subtypes, and inhibit serotonin-evoked smooth muscle contractions of the rat gastric fundus and the rabbit aorta. The chemical name of serotonin is 3-(2-aminoethyl)-1H-indol-5-ol.

$5\text{-HT}_{2A}$ and $5\text{-HT}_{2C}$ receptor binding studies $5\text{-HT}_{2A}$ and $5\text{-HT}_{2C}$ receptor binding was measured according to the methods described by Leysen et al. /Mol.

Pharmacol., 21, 301 (1981)/ and Pazos et al. /Eur. J. Pharmacol., 106, 539 (1985)/, respectively. 5-$HT_{2A}$ receptor binding was measured in rat brain frontal cortex membrane preparation using tritiated ketanserine /3-/2-(4-fluorobenzoyl)- -1-piperidinyl/ethyl-2,4-(1H,3H)-quinazoline-dione/(60–90 Ci/mmole) as ligand. 5-$HT_{2C}$ receptor binding was measured in pig brain choroid plexus membrane preparation using tritiated mesulergine /N'-/(8)-1,6-dimethyl-ergoline-8-yl/-N,N-dimethylsulfamide (70–85 Ci/mmole) as the ligand. Non-specific binding to 5-$HT_{2A}$ and 5-$HT_{2C}$ receptors were determined in the presence of 10 micro M cyproheptadine/4-(5H-dibenzo/a,d/cycloheptene-5-ylidene)-1-methylpiperidine/ and 1 micro M mianserine/1,2,3,4,10,14b-hexahydro-2-methyldibenzo-/c,f/pyrazino/1,2-a/azepine/, respectively. The final incubation volumes were 250 and 1000 microlitres. Samples were incubated for 15 and 30 minutes at 37° C. Incubation was stopped by adding 9 ml of ice-cold 50 mM tris(hydroxymethyl)-aminomethane hydrochloride (pH=7.7) to the reaction mixture. The samples were rapidly filtered through Whatman GF/B glass fiber filters using reduced pressure. Before use, the filters were soaked in a 0.05% poly-ethyleneimine solution for 2 to 3 hours. Radioactivity of the filters was determined by a scintillation spectrometer.

The results obtained are shown in Table I.

TABLE I

Effect of the compounds examined On 5-$HT_{2A}$ and 5-$HT_{2C}$ receptors

| Compound (Example No.) | Inhibition of receptor binding of the radioactive ligand ($K_i$ in nm/l) | |
|---|---|---|
| | 5-$HT_{2C}$ | 5-$HT_{2A}$ |
| 3 | >100 | 58 |
| 5 | 67 | 16 |
| 12 | 47 | >100 |
| 13 | 12 | 20 |
| 14 | >100 | 78 |
| 19 | >100 | 48 |
| 20 | >100 | 203 |
| 21 | 39 | >100 |
| 22 | >100 | 56 |
| 23 | >100 | 20 |
| 24 | 22 | 18 |
| 25 | >100 | 20 |
| 26 | 45 | 48 |
| 28 | 50 | >100 |
| 31 | 21 | >100 |
| 34 | >100 | 71 |
| 35 | 69 | >100 |
| 36 | 18 | >100 |
| 39 | 27 | not tested |
| 40 | >100 | 21 |
| 44 | >100 | 93 |
| 45 | 25 | 27 |
| 47 | 33 | >100 |
| 53 | >100 | 15 |
| 56 | 57 | 38 |
| 57 | 42 | >100 |
| 65 | 42 | 34 |
| 66 | >100 | 61 |
| 67 | 8.6 | 4.6 |
| 68 | >100 | 21 |
| 69 | 26 | 38 |
| 72 | 20 | 24 |
| 101 | 24 | 16 |

From Table I it can be seen that the compounds of the formula I have considerable affinity for 5-$HT_{2A}$ and 5-$HT_{2C}$ receptors.

Inhibition of serotonin-induced contractions of rat stomach fundus smooth muscle The experiments were performed on male Wistar rats weighing 350 to 400 g. The animals were fasted for 24 hours before the experiments, however, they were allowed to drink tap water ad libitum. The method used was a modified version of Vane et al. /J. Pharmac. Chemother., 12, 344 (1957)/. The rats were killed by decapitation and their stomach was removed, and 3 mm wide and 20 to 30 mm long strips were cut in parallel with the greatest curvature of the stomach. The strips were incubated for 60 minutes in a 6 ml Lucite chamber filled with Tyrode solution (NaCl 136.9 mM, $KCl_{2.7}$ mM, $CaCl_2$ 1.8 mM, $MgCl_2$ 1.0 mM, $NaHCO_3$ 11.9 mM, glucose 5.6 mM, $NaH_2PO_4$ 0.4 mM) warmed to 37° C. and bubbled with a gas consisting of 95% of oxygen and 5% of carbon dioxide. The strips were stretched with 0.5 g during the 60 minutes equilibration time and were washed every 20 minutes. The tension was measured isometrically by a strain gauge (Hugo Sachs) and was recorded on a Graphtech Mark VII 3101 polygraph.

Experimental protocol:

Three control contractions were evoked by 5-HT added to the bath in $10^{-7}$M concentration (C1, C2, C3).

If peak tension did not differ more than by 10% between C2 and C3, a threshold concentration of the compound to be tested was added to the bath and the strip was contracted by 5-HT ($10^{-7}$M) in its presence (T1).

The effects of the test compounds were determined in 5 increasing concentrations (T2, T3, T4, T5, and T6). After determining the effect of two concentrations of the test compounds, the control 5-HT response was checked after each test measurement.

Results and evaluation:

$IC_{50}$ was calculated by nonlinear curve fitting of the inhibitory effect of increasing concentrations of the test compound.

The compounds of the invention inhibit the 5-HT-evoked contractions of the isolated rat stomach fundus smooth muscle strips. The results obtained are shown in Table II.

TABLE II

Inhibition of 5-HT-evoked contractions of isolated rat stomach fundus

| Compound (Example No.) | Inhibition, $IC_{50}$ (micro M/1) |
|---|---|
| 20 | 0.56 |
| 22 | 0.32 |
| 48 | 0.42 |
| 57 | 0.89 |
| 64 | 0.68 |

Determination of 5-$HT_{2A}$ receptor antagonistic effect on isolated rabbit aorta New-Zealand, male, white rabbits weighing 2.0 to 2.5 kg were killed by a blow on the head. The thoracic aorta segment after the aortic arch was removed and placed into a Krebs' solution (NaCl 118 mM, KCl 4.6 mM, $NaHCO_3$ 25 mM, glucose 10.5 mM, $Mg_3(SO_4)_2$ 1 mM, $KH2PO_4$ 1 mM, $CaCl_2$ 2.6 mM). The aorta was carefully cleaned from fat and connective tissue, and was cut into 3 mm wide and 30 mm long helical strips. Four strips were obtained from each rabbit. The strips were equilibrated at 37° C. for 60 minutes in an organ chamber filled with Krebs' solution. The strips were also oxygenated by bubbling carbogen gas (5% of carbon dioxide and 95% of oxygen) through the solution. The strips were stretched by 1 g tension.

The contractions were measured by a Hugo Sachs K-30 type strain gauge, and were registered on a Multicorder type polygraph. During the last 40 minutes of the equilibration, the MAO enzym inhibitor tranylcypramine ($10^{-7}$M) /chemical name: (±)-trans-2-phenylcyclopropylamine/ was also added to the bath.

Any alpha-adrenergic effects of the test compounds were eliminated by $10^{-8}$M of phenoxybenzamine /N-(2-chloroethyl)-N-(1-methyl-2-phenoxyethyl)benzylamine/ /Clancy et al., J. Pharm. Exp. Ther., 233, 761 (1985). Testing of the serotonergic antagonistic effect was started at the 90th minute of incubation. The stability and reproducibility of the contractile response of the aortic strips to serotonin was tested by two consecutive application and wash-out procedures of $10^{-6}$M concentration of 5-HT, 40 minutes apart. Measurements were continued only in the case if peak tensions in the above test did not differ by more than 10%. 30 minutes after the second testing, a preset concentration of the test compound was added to the bath, and, after a 10 minutes incubation time, the response to $10^{-6}$M of 5-HT was determined in the presence of the compound to be tested.

Two different concentrations of a given compound were tested on each aortic strip by the above method. Reproducibility of the control 5-HT-evoked response was checked between testing the two concentrations of the compound. The second concentration was tested only if the 5-HT-evoked tension did not differ by more than ±10% from the original control response.

$IC_{50}$ was calculated by nonlinear curve fitting of the inhibitory effect of increasing concentrations of the test compound. The results obtained are shown in Table III.

TABLE III

Inhibition of 5-HT-evoked contractions on isolated rabbit aortic strips

| Compound (Example No.) | Inhibition, $IC_{50}$ (micro M/l) |
|---|---|
| 3 | 0.96 |
| 5 | 0.25 |
| 13 | 0.12 |
| 14 | 6.0 |
| 20 | 1.5 |
| 22 | 0.42 |
| 23 | 0.67 |
| 24 | 0.24 |
| 25 | 0.28 |
| 26 | 0.26 |
| 27 | 0.9 |
| 31 | 0.73 |
| 39 | 0.3 |
| 44 | 0.65 |
| 45 | 0.43 |
| 53 | 0.47 |
| 54 | 0.57 |
| 56 | 0.9 |
| 57 | 0.89 |
| 65 | 0.17 |
| 67 | 0.039 |
| 68 | 0.78 |
| 69 | 0.096 |
| 72 | 0.084 |

Based on the results presented in Table III, it can be stated that the compounds of the invention effectively inhibit the serotonin-evoked contractions of the isolated rabbit aortic preparation.

Based on the results of the above studies, the novel compounds of the formula I can be applied for the treatment of various disorders due to pathological alterations of the central nervous system.

The compounds of the formula I demonstrated inhibitory activity primarily at $5-HT_{2A}$ and $5-HT_{2C}$ serotonergic receptor subtypes. Based on literature data, these receptors play a fundamental role in the pathomechanism of anxiety disorders, schizophrenia and migraine. The $5-HT_{2C}$ receptor agonist m-chlorophenylpiperazine/Conn et al., Proc. Natl. Acad. Sci. USA, 83, 4086 (1986)/ induces anxiety both in rats /Kennett et al., Eur. J. Pharmacol., 164, 455 (1989)/ and human beings /Kahn and Weltzer, Biol. Psychiat., 30, 1139 (1991)/. Based on studies performed in rats, the anxiogenic effect of m-chlorophenylpiperazine can be attributed to the activation of $5-HT_{2C}$ (formerly $5-HT_{1C}$) receptors /Kennett et al., Eur. J. Pharmacol., 164, 455 (1989)/. Compounds with antagonistic effect at the $5-HT_{2A/2C}$ receptors have been shown to be anxiolytic in animal experiments /Kennett, Psychopharmacol., 107, 379 (1992)/.

The $5-HT_{2A/2C}$ receptor antagonistic compound ritanserin /chemical name: 6-[2-14-bis(4-fluorophenyl)methylene/-1-piperidinyl-ethyl]-7-7-methyl-5H-thiazolo/3,2-a/pirimidine-5-one/ has been proved to be effective for the treatment of different forms of human anxiety /Ceulemans et al., Pharmacopsychiat., 18, 303 (1985)/. Usefulness of $5-HT_{2A}$ receptor antagonists for neuroleptic indication is proved by the fact that a basic role is attributed to the $5-HT_{2A}$ antagonistic effect in the therapeutic efficacy of clozapine/chemical name: 8-chloro-11-(4-methyl-1-piperazinyl)-5H-dibenzo/b,e//1,4/-diazepine/, a widely used neuroleptic compound/Meltzer, J. Clin. Psychiatry, 55 Suppl. B, 47 (1994)/.

Usefulness of the compounds of the invention for prophylactic treatment of migraine is supported by both the $5-HT_{2A/2C}$ receptor antagonistic properties of the compounds /Sleight et al. in Serotonin Receptor Subtypes: Basic and Clinical Aspects, ed. Peroutka, S. J., pp. 211, Wiley-Liss Inc., (1991)/ and their activity exhibited in rat stomach fundus test.

Besides central nervous system disorders, the compounds of the invention can be useful for the treatment of ischemic heart disease. Results of the rabbit aorta test make it probable that the compounds can have $5-HT_2$ antagonistic effect also on the heart vessels and the myocardium. It is known that $5-HT_2$ receptor antagonists play a role in the development of heart disease. $5-HT_2$ receptor antagonistic compounds also improve contractility and accelerate regeneration of the myocardium after an ischemic insult/Grover et al., J. Cardiovasc. Pharmacol., 22, 664 (1993)/.

A role of serotonergic receptors is assumed in the regulation of food consumption and body temperature as well as development of depression, addiction to drugs and alcohol, some other gastroenterologic and circulatory disorders, and in the pathomechanism of pain/Sleight et al. in Serotonin Receptor Subtypes: Basic and Clinical Aspects, ed. Peroutka, S. J., pp. 211, Wiley-Liss Inc., (1991); Kennett, Drugs, 125 (1993)/.

Due to the above test results, the novel compounds of the formula I or pharmaceutically acceptable acid addition salts thereof can be used as active ingredients of pharmaceutical compositions. The pharmaceutical compositions of the invention contain a therapeutically active amount of the compound of the formula I or a pharmaceutically acceptable acid addition salt thereof and one or more conventional carrier(s).

The pharmaceutical compositions of the invention are suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethyleneglycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propyleneglycol, ethanol etc.; preservatives such as methyl p-hydroxybenzoate etc. as the carrier.

Pharmaceutical compositions suitable for parenteral administration consist of steril solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical compositions of the invention contain, in general, 0.1 to 95.0 per cent by mass of a compound of the formula I or a pharmaceutically acceptable acid addition salt thereof. A typical dose for adult patients amounts to 0.1 to 20 mg of the compound of the formula I or a pharmaceutically acceptable acid addition salt thereof, daily. The above dose can be administered in one or more portions. The actual dosage depends on many factors and is determined by the doctor.

The pharmaceutical compositions of the invention are prepared by admixing a compound of the formula I or a pharmaceutically acceptable acid addition salt thereof to one or more carrier(s), and converting the mixture obtained to a pharmaceutical composition in a manner known per se. Useful methods are known from the literature, e.g. Remington's Pharmaceutical Sciences.

Suitably, the pharmaceutical compositions of the invention contain a compound of the formula I, wherein $R^1$ and $R^3$ represent, independently, a hydrogen, a methyl group, an amino group, an acetylamino group or a phenyl group optionally bearing 1 to 3 substituents selected from the group consisting of, independently, a chloro. a methoxy group, a dimethylamino group or a benzyloxy group, $R^2$ stands for a hydrogen, a cyano group, a furylmethyl group, a cyclohexylmethyl group, an ethoxycarbonyl group, a hydroxyethyl group or a benzyl group optionally bearing 1 to 3 substituents selected from the group consisting of, independently, a chloro, a fluoro, a $C_{1-3}$ alkyl group, a methoxy group, a trifluoro--methyl group, a hydroxy group, a benzyloxy group or a dimethylamino group.

$R^4$ means a hydrogen, or $R^3$ forms with $R^4$ an oxygen atom, $R^5$ is a hydrogen, or $R^4$ forms with $R^5$ a valence bond, $R^6$ represents a chloro, a fluoro, a cyano group, a nitro group, a methyl group, a methoxy group or a trifluoro methyl group, m has a value of 0 or 1, n has a value of 1 or 2, p has a value of 2 or 11, and k has a value of 0, 1, 2 or 3, and pharmaceutically acceptable acid addition salts thereof as the active ingredient.

Preferably, the pharmaceutical compositions of the invention contain a compound of the formula I, wherein $R^1$ and $R^3$ represent an amino group, $R^2$ stands for a hydrogen or a benzyl group optionally bearing 1 to 3 substituents selected from the group consisting of, independently, a fluoro, a chloro, a methoxy group and a dimethylamino group;

$R^4$ forms with $R^5$ a valence bond, $R^6$ means a fluoro, a chloro, a nitro group, a cyano group, a methyl group, a methoxy group or a trifluoromethyl group, k has a value of 1, m has a value of 1, n has a value of 1, and p has a value of 2, and pharmaceutically acceptable acid addition salts thereof as the active ingredient.

Furthermore, the invention refers to a method for the treatment of diseases especially due to pathological alterations of the central nervous system. The method of the invention comprises administering an effective non-toxic dose of a compound of the formula I or a pharmaceutically acceptable acid addition salt thereof to a patient suffering from said diseases.

The invention also refers to the use of a compound of the formula I or a pharmaceutically acceptable acid addition salt thereof for the preparation of a pharmaceutical composition.

The invention is further elucidated by means of the following Examples.

General method for preparing compounds of the formula I 0.05 moles of a mercaptopyrimidine of the formula II or an alkali metal salt thereof, 6.9 g (0.05 moles) of potassium carbonate and 0.83 g (0.005 moles) of potassium iodide are stirred in 300 ml of solvent at room temperature for 15 minutes, and, to the mixture obtained, 0.05 moles of haloalkylpiperazine of the formula III or an acid addition salt thereof are added. If the solvent consists of methanol or ethanol, the reaction mixture is boiled under reflux, while if the solvent is dimethylformamide, the reaction mixture is heated at 65 to 70° C. for the time given in the Examples. After the lapse of the reaction time, the mixture is worked up by one of the following methods.

Method "A":

The inorganic salts separated are filtered, then the filtrate is evaporated under reduced pressure.

Method "B":

The reaction product separated is filtered together with the inorganic salt, then latter is removed by washing with water.

Method "C":

The reaction mixture is poured onto 300 ml of water to dissolve the inorganic salts, then the product separated is filtered.

The reaction product obtained by any of the above methods is purified as indicated in the Examples.

Using the above general method, the following compounds of the formula I were prepared:

EXAMPLE 1
2-[2-/4-(2-Chlorobenzyl)-1-piperazinyl/-ethylthio]pyrimidine

Solvent employed in the reaction: methanol.
Reaction time: 3 hours. The reaction mixture is worked up by flash chromatography using a mixture of chloroform and methanol in a ratio of 99:1 as the eluent.
Yield: 4 g (23%).
Melting point: oil.
Analysis for $C_{17}H_{21}ClN_4S$ (348.90)
Calculated: C 58.53%, H 6.07%, Cl 10.16%, N 16.06%, S 9.18%;
Found: C 58.13%, H 6.25%, Cl 9.97%, N 15.73%, S 8.98%.

EXAMPLE 2
2-/2-(4-Benzyl-1-piperazinyl)ethylthio/-4,6-diaminopyrimidine

Solvent employed in the reaction: methanol.
Reaction time: 3 hours. The reaction mixture is worked up by method "B".
Yield: 11.2 g (65%).
Purification: recrystallization from aqueous ethanol.
Melting point: 167–169° C.
Analysis for $C_{17}H_{42}N_6S$ (344.485)
Calculated: C 59.27%, H 7.02%, N 24.40%, S 9.31%;
Found: C 58.78%, H 6.85%, N 24.20%, S 9.31%.

EXAMPLE 3
2-[2-/4-(4-Fluorobenzyl)-1-piperazinyl/-ethylthio]-7-4,6-diaminopyrimidine Solvent employed in the reaction: methanol.
Reaction time: 3 hours. The reaction mixture is worked up by method "A".
Yield: 8.2 g (45%).
Purification: recrystallization from aqueous ethanol.
Melting point: 179–182° C.
Analysis for $C_{17}H_{23}FN_6S$ (362.475)
Calculated: C 56.25%, H 6.32%, N 23.19%, S 8.93%;
Found: C 56.33%, H 6.40%, N 23.19%, S 8.84%.

EXAMPLE 4
2-[2-/4-(4-Chlorobenzyl)l-piperazinyl/-ethylthio]-4,6-diaminopyrimidine Solvent employed in the reaction: methanol.
Reaction time: 3 hours. The reaction mixture is worked up by method "A".
Yield: 17.5 g (92%).
Purification: recrystallization from aqueous methanol.
Melting point: 192–194° C.
Analysis for $C_{17}H_{23}ClN_6S$ (378.930)
Calculated: C 53.89%, H 6.12%, Cl 9.36%, N 22.18%, S 8.46%;
Found: C 53.45%, H 6.25%, Cl 9.26%, N 22.35%, S 8.59%.

EXAMPLE 5
2-[2-/4-(2-Chlorobenzyl)-1-piperazinyl/-ethylthio]-4,6-diaminopyrimidine Solvent employed in the reaction: methanol.
Reaction time: 3 hours. The reaction mixture is worked up by method "A".
Yield: 9.5 g (50%).
Purification: recrystallization from aqueous ethanol.
Melting point: 150–153° C.
Analysis for $C_{17}H_{23}ClN_6S$ (378.930)
Calculated: C 53.89%, H 6.12%, Cl 9.36%, N 22.18%, S 8.46%;
Found: C 53.45%, H 6.25%, Cl 9.50%, N 22.18%, S 8.41%.

EXAMPLE 6
2-[2-/4-(4-Nitrobenzyl)-1-piperazinyl/-ethylthio]-4,6-diaminopyrimidine Solvent employed in the reaction: methanol.
Reaction time: 3 hours. The reaction mixture is worked up by method "B".
Yield: 17.5 g (90%).
Purification: recrystallization from methanol.
Melting point: 218–219° C.
Analysis for $C_{17}H_{23}N_7O_2S$ (389.483)
Calculated: C 52.43%, H 5.95%, N 25.17%, S 8.23%;
Found: C 52.10%, H 6.17%, N 24.54%, S 8.04%.

EXAMPLE 7
2-[2-/4-(2-Nitrobenzyl)-1-piperazinyl/-ethylthio]-7–4,6-diaminopyrimidine Solvent employed in the reaction: methanol.
Reaction time: 3 hours. The reaction mixture is worked up by method "A".
Yield: 8.6 g (44%)
Purification: recrystallization from aqueous ethanol.
Melting point: 165–169° C.
Analysis for $C_{17}H_{23}N_7O_2S$ (389.483)
Calculated: C 52.43%, H 5.95%, N 25.17%, S 8.23%;
Found: C 52.19%, H 5.94%, N 24.33%, S 8.07%.

EXAMPLE 8
2-[3-/4-(4-Nitrobenzyl)-1-piperazinyl/-propylthio]-4,6-diaminopyrimidine Solvent employed in the reaction: methanol.
Reaction time: 3 hours. The reaction mixture is worked up by method "A".
Yield: 6.5 g (32%).
Purification: recrystallization from aqueous dimethylformamide.
Melting point: 186–188° C.
Analysis for $C_{18}H_{25}N_7O_2S$ (403.510)
Calculated: C 53.38%, H 6.25%, N 24.30%, S 7.95%;
Found: C 54.01%, H 6.26%, N 23.62%, S 7.72%.

EXAMPLE 9
2-[2-/4-(2,4-Dinitrophenyl)-1-piperazinyl/-ethylthio]-4,6-diaminopyrimidine Solvent employed in the reaction: methanol.
Reaction time: 3 hours. The reaction mixture is worked up by method "C".
Yield: 17.2 g (82%).
Purification: treatment with water. acetone, then chloroform.
Melting point: 235–237° C.
Analysis for $C_{16}H_{20}N_8O_4S$ (420.453)
Calculated: C 45.71%. H 4.79%, N 26.65%, S 7.63%;
Found: C 45.75%. H 4.59%, N 27.71%, S 7.29%.

EXAMPLE 10
2-[2-/4-(4-Trifluoromethyl-2,6-dinitro-phenyl)-1-piperazinyl/ethylthio]-4,6-diaminopyrimidine Solvent employed in the reaction: methanol.
Reaction time: 3 hours. The reaction mixture is worked up by method "C".
Yield: 20.3 g (83%).
Purification: recrystallization from ethanol.
Melting point: 195–196° C.
Analysis for $C_{17}H_{19}F_3N_8O_4S$ (488.451)
Calculated: C 41.80%. F 11.67%, N 22.94%, S 6.56%;

Found: C 41.08%, H 4.10%, F 11.37%, N 22.53%. S 6.76%.

EXAMPLE 11

2-[2-/4-(4-nitrobenzyl)-1-piperazinyl/-ethylthio]-4,6-diamino-5-(2-furylmethyl)-pyrimidine Solvent employed in the reaction: methanol.

Reaction time: 3 hours. The reaction mixture is worked up by method "B".

Yield: 14 o (50%).

Purification: chromatography on a column filled with Kieselgel 60 and elution with acetone, then recrystallization from ethanol.

Melting point: 157–159° C.

Analysis for $C_{22}H_{27}N_7O_3S$ (469.6)

Calculated: C 56.27%, H 5.80%, N 20.88%, S 6.83%;

Found: C 54.26%, H 5.81%. N 20.18%. S 6.69%.

EXAMPLE 12

2-[2-/4-(3-Methdxybenzyl)-1-piperazinyl/-ethylthio]-4,6-diamino-5-benzylpyrimidine Solvent employed in the reaction: methanol.

Reaction time: 3 hours. The reaction mixture is worked us by method "A".

Yield: 12.6 g (54%).

Purification: recrystallization from aqueous ethanol.

Melting point: 143–145° C.

Analysis for $C_{25}H_{32}N_6OS$ (464.637)

Calculated: C 64.49%, H 7.14%, N 18.05%, S 6.89%;

Found: C 64.67%r H 6.98%, N 17.84%, S 6.95%.

EXAMPLE 13

2-[2-/4-(2-Chlorobenzyl)-1-piperazinyl/-ethylthio]-4,6-diamino-5-benzylpyrimidine Solvent employed in the reaction: methanol.

Reaction time: 3 hours. The reaction mixture is worked up by method "B".

Yield: 14.5 g (62%).

Purification: recrystallization from aqueous ethanol.

Melting point: 177–180° C.

Analysis for $C_{24}H_{29}ClN_6S$ (469.056)

Calculated: C 61.46%, 11 6.23%, Cl 7.55%, N 17.92%, S 6.83%;

Found: C 60.85%, H 6.20%, Cl 7.54%, N 17.46%, S 6.56%.

EXAMPLE 14

2-[2-/4-(4-Nitrobenzyl)-1-piperazinyl/-ethylthio]-4,6-diamino-5-benzylpyrimidine Solvent employed in the reaction: methanol.

Reaction time: 3 hours. The reaction mixture is worked up by method "B".

Yield: 17.5 g (73%).

Melting point: 188–191 C.

Analysis for $C_{24}H_{29}N_7O_2S$ (479.608)

Calculated: C 60.10%, H 6.10%, N 20.44%, S 6.68%;

Found: C 59.25%, H 6.10%, N 19.92%, S 6.43%.

EXAMPLE 15

2-[2-/4-(3-Trifluoromethylbenzyl)-1-piperazinyl/ethylthio]-7-4,6-diamino-5-benzylpyrimidine Solvent employed in the reaction: methanol.

Reaction time: 3 hours. The reaction mixture is worked up by method "A".

Yield: 20.6 g (82%).

Purification: recrystallization from aqueous ethanol.

Melting point: 179–180° C.

Analysis for $C_{25}H_{29}F_3N_6S$ (502.609)

Calculated: C 59.62%, H 6.00%, N 16.69%, S 6.37%;

Found: C 59.72%, H 5.57%, N 17.01%, S 6.23%.

EXAMPLE 16

2-[2-/4-(2,6-Dinitro-4-trifluoromethyl-phenyl)-1-piperazinyl/ethylthio]-4,6-diamino-5-benzylpyrimidine Solvent employed in the reaction: methanol.

Reaction time: 3 hours. The reaction mixture is worked up by method "A".

Yield: 13 g (45%).

Purification: chromatography on a column filled with Kieselgel 60 and elution with ethyl acetate.

Melting point: 159–163° C.

Analysis for $C_{24}H_{25}F_3N_8O_4S$ (578.577)

Calculated: C 49.82%, H 4.36%, N 19.37%, S 5.54%, F 9.85%;

Found: C 49.36%, H 4.33%, N 18.54%, S 5.76%, F 9.85%.

EXAMPLE 17

2-[2-/4-(4-Nitrobenzyl)-1-piperazinyl/-ethylthio]4,6-diamino-5-(cyclohexylmethyl)-pyrimidine Solvent employed in the reaction: methanol.

Reaction time: 3 hours. The reaction mixture is worked up by method "A".

Yield: 9.7 g (40%).

Purification: chromatography on a column filled with Kieselgel 60 and elution with acetone, then recrystallization from ethanol.

Melting point: 160–162° C.

Analysis for $C_{24}H_{35}N_7O_2S$ (485.656)

Calculated: C 59.36%, H 7.26%, N 20.19%, S 6.60%;

Found: . C 59.65%, H 7.20%, N 19.90%, S 6.57%

EXAMPLE 18

2-[2-/4-(2,6-Dinitro-4-trifluoromethyl-phenyl)-1-piperazinyl/ethylthio]-4,6-diamino-5-(cyclohexylmethyl)pyrimidine Solvent employed in the reaction: methanol.

Reaction time: 3 hours. The reaction mixture is worked up by method "C".

Yield: 11.1 g (38%).

Purification: chromatography on a column filled with Kieselgel 60 and elution with ethyl acetate.

Melting point: 176–178° C.

Analysis for $C_{24}H_{31}F_3N_8O_4S$ (584.625)

Calculated: C 49.31%, H 5.34%, N 19.17%, S 5.48%, F 9.75%;

Found: C 48.80%, H 5.28%t N 18.80%, S 5.60%, F 10.19%.

EXAMPLE 19

2-[2-/4-(4-Nitrobenzyl)-1-piperazinyl/-ethylthio]-4,6-diamino-5-(2-hydroxybenzyl)-pyrimidine Solvent employed in the reaction: methanol.

Reaction time: 3 hours. The reaction mixture is worked up by method "A".

Yield: 9.9 g (4Q %).

Purification: flash chromatography using a mixture of chloroform and methanol in a ratio of 8:2 as the eluent.

Melting point: 195–199° C.

Analysis for $C_{24}H_{29}N_7O_3S$ (495.608)

Calculated: C 58.16%, H 5.90%, N 19.78%, S 6.47%;

Found: C 60.26%, H 6.08%, N 19.97%, S 6.55%.

EXAMPLE 20
2-[2-/4-(4-Nitrobenzyl)-1-piperazinyl/-ethylthio]-4,6-diamino-5-(4-fluorobenzyl)-pyrimidine
Solvent employed in the reaction: methanol.
Reaction time: 3 hours. The reaction mixture is worked up by method "B".
Yield: 5.5 g (47%).
Purification: recrystallization from aqueous ethanol.
Melting point: 201–203° C.
Analysis for $C_{24}H_{28}FN_7O_2S$ (497.599)
Calculated: C 57.93%, H 5.67%, N 19.70%, S 6.44%;
Found: C 57.53%, H 5.66%, N 19.55%, S 6.60%.

EXAMPLE 21
2-[2-/4-(3-Trifluoromethylbenzyl)-1-piperazinyl/ethylthio] 4,6-diamino-5-(4-fluorobenzyl)pyrimidine
Solvent employed in the reaction: methanol.
Reaction time: 3 hours. The reaction mixture is worked up by method "A".
Yield: 20.6 g (79%).
Purification: recrystallization from aqueous ethanol.
Melting point: 162–164° C.
Analysis for $C_{25}H_{28}F_4N_6S$ (520.600)
Calculated: C 57.68%, H 5.42%, N 16.14%, S 6.16%;
Found: C 57.08%, H 5.34%, N 16.36%, S 6.11%.

EXAMPLE 22
2-/2-(4-Benzyl-1-piperazinyl)ethylthio/-4,6-diamino-5-(4-methoxybenzyl)pyrimidine
Solvent employed in the reaction: methanol.
Reaction time: 3 hours. The reaction mixture is worked up by method "B".
Yield: 21.8 g (94%).
Melting point: 152–154° C.
Analysis for $C_{25}H_{32}N_6OS$ (464.637)
Calculated: C 64.63%, H 6.94%, N 18.09%, S 6.90%;
Found: C 63.11%, H 6.86%, N 17.77%, S 6.76%.

EXAMPLE 23
2-[2-/4-(4-Methylbenzyl)-1-piperazinyl/-ethylthio]-4,6-diamino-5-(4-methoxybenzyl)-pyrimidine
Solvent employed in the reaction: methanol.
Reaction time: 3 hours. The reaction mixture is worked up by method "A".
Yield: 16.3 g (68%).
Purification: recrystallization from aqueous ethanol.
Melting point: 183–185° C.
Analysis for $C_{26}H_{34}N_6OS$ (478.664)
Calculated: C 65.24%, H 7.16%, N 17.56%, S 6.70%;
Found: C 64.52%, H 6.95%, N 17.70%, S 6.49%.

EXAMPLE 24
2-[2-/4-(2-Methylbenzyl)-1-piperazinyl/-ethylthio]-4,6-diamino-5-(4-methoxybenzyl)-pyrimidine
Solvent employed in the reaction: methanol.
Reaction time: 3 hours. The reaction mixture is worked up by method "A".
Yield: 18.4 g (77%).
Purification: recrystallization from aqueous ethanol.
Melting point: 166–168° C.
Analysis for $C_{26}H_{34}N_6OS$ (478.664)
Calculated: C 65.24%, H 7.16%, N 17.56%, S 6.70%;
Found: C 64.63%, H 7.30%, N 17.47%, S 6.90%.

EXAMPLE 25
2-[2-/4-(2-Fluorobenzyl)-1-piperazinyl/-ethylthio]-4,6-diamino-5-(4-methoxybenzyl)-pyrimidine
Solvent employed in the reaction: methanol
Reaction time: 3 hours. The reaction mixture is worked up by method "A".
Yield: 20.5 g (85%).
Purification: recrystallization from aqueous ethanol.
Melting point: 162–164° C.
Analysis for $C_{25}H_{31}FN_6OS$ (482.628)
Calculated: C 62.22%t H 6.47%, N 17.41%, S 6.64%;
Found: C 62.17%, H 6.68%, N 17.42%, S 6.64%.

EXAMPLE 26
2-[2-/4-(3-Cyanobenzyl)-1-piperazinyl/-ethylthio]-4,6-diamino-5-(4-methoxybenzyl)-pyrimidine
Solvent employed in the reaction: methanol.
Reaction time: 3 hours. The reaction mixture is worked up by method "A".
Yield: 21.3 g (87%).
Purification: flash chromatography using a mixture of chloroform and methanol in a ratio of 9:1 as the eluent.
Melting point: 142–144° C.
Analysis for $C_{26}H_3N_7OS$ (489.647)
Calculated: C 63.78%, H 6.38%, N 20.02%, S 6.55%;
Found: C 63.32%, H 6.31%, N 20.34%, S 6.43%.

EXAMPLE 27
2-[2-/4-(2-Cyanobenzyl)-1-piperazinyl/-ethylthio]-4,6-diamino-5-(4-methoxybenzyl)-pyrimidine
Solvent employed in the reaction: methanol.
Reaction time: 3 hours. The reaction mixture is worked up by method "A".
Yield: 21.3 g (87%).
Purification: recrystallization from aqueous ethanol.
Melting point: 150–153° C.
Analysis for $C_{26}H_{31}N_7OS$ (489.647)
Calculated: C 64.36%, H 6.43%, N 20.08%, S 6.57%;
Found: C 63.78%, H 6.38%, N 20.02%, S 6.55%.

EXAMPLE 28
2-[2-/4-(3-Methoxybenzyl)-1-piperazinyl/-ethylthio]-4,6-diamino-5-(4-methoxybenzyl)-pyrimidine
Solvent employed in the reaction: methanol.
Reaction time: 3 hours. The reaction mixture is worked up by method "A".
Yield: 18.8 g (76%).
Purification: recrystallization from aqueous ethanol.
Melting point: 150–152° C.
Analysis for $C_{26}H_{34}N_6O_2S$ (494.664)
Calculated: C 63.13%, H 6.93%, N 16.99%, S 6.48%;
Found: C 62.86%, H 6.98%, N 17.15%, S 6.68%.

EXAMPLE 29
2-[2-/4-(4-Methoxybenzyl)-1-piperazinyl/-ethylthio]-4,6-diamino-5-(4-methoxybenzyl)-pyrimidine
Solvent employed in the reaction: methanol.
Reaction time: 3 hours. The reaction mixture is worked up by method "A".
Yield: 17.8 g (72%).
Purification: recrystallization from aqueous ethanol.
Melting point: 156–158° C.
Analysis for $C_{26}H_{34}N_6O_2S$ (494.664)
Calculated: C 63.13%, H 6.93%, N 16.99%, S 6.48%;
Found: C 63.50%, H 7.23%, N 16.31%, S 6.66%.

EXAMPLE 30
2-[2-/4-(4-Methoxybenzyl)-1-piperazinyl/-ethylthio]-4,6-diamino-5-(2-methoxybenzyl)-pyrimidine
Solvent employed in the reaction: methanol.
Reaction time: 3 hours. The reaction mixture is worked up by method "A".

Yield: 20.0 g (81%).

Purification: flash chromatography using a mixture of chloroform and methanol in a ratio of 9:1 as the eluent.

Melting point: 149–152° C.

Analysis for $C_{26}H_{34}N_6O_2S$ (494.464)

Calculated: C 63.13%, H 6.93%, N 16.99%, S 6.48%;

Found: C 60.83%, H 6.74%, N 16.55%, S 6.16%.

EXAMPLE 31

2-[2-/4-(3-Methoxybenzyl)-1-piperazinyl/-ethylthio]-4,6-diamino-5-(2-methoxybenzyl)-pyrimidine Solvent employed in the reaction: methanol.

Reaction time: 3 hours. The reaction mixture is worked up by method "A".

Yield: 22 g (89%).

Purification: flash chromatography using a mixture of chloroform and methanol in a ratio of 9:1 as the eluent.

Melting point: 118–120° C.

Analysis for $C_{26}H_{34}N_6O_2S$ (494.664)

Calculated: C 63.13%, H 6.93%, N 16.99%, S 6.48%;

Found: C 61.89%, H 6.84%, N 17.17%, S 6.26%.

EXAMPLE 32

2-[2-/4-(4-Chlorobenzyl)-1-piperazinyl/-ethylthio]-4,6-diamino-5-(4-methoxybenzyl)-pyrimidine Solvent employed in the reaction: methanol.

Reaction time: 3 hours. The reaction mixture is worked up by method "A".

Yield: 11.5 g (46%).

Purification: recrystallization from aqueous ethanol.

Melting point: 185–187° C.

Analysis for $C_{25}H_{31}ClN_6OS$ (499.082)

Calculated: C 60.17%, H 6.26%, Cl 7.10%, N 16.84%, S 6.42%;

Found: C 58.32%, H 6.19%, Cl 6.95%, N 17.10%, S 6.42%.

EXAMPLE 33

2-[2-/4 (4-Nitrobenzyl)-1-piperazinyl/-ethylthio]-4,6-diamino-5-(4-methoxy-benzyl)pyrimidine Solvent employed in the reaction: methanol.

Reaction time: 3 hours. The reaction mixture is worked up by method "A".

Yield: 25.2 g (99%).

Purification: recrystallization from aqueous acetone.

Melting point: 191–193° C.

Analysis for $C_{25}H_{31}N_7O_3S$ (509.635)

Calculated: C 58.92%, H 6.13%, N 19.24%, S 6.29%;

Found: C 58.20%, H 6.08%, N 18.65%, S 6.14%.

EXAMPLE 34

2-[2-/4-(4-Nitrobenzyl)-1-piperazinyl/-ethylthio]-4,6-diamino-5-(2-methoxy-benzyl)pyrimidine Solvent employed in the reaction: methanol.

Reaction time: 3 hours. The reaction mixture is worked up by method "A".

Yield: 12.2 g (48%).

Purification: flash chromatography using a mixture of acetonitrile and methanol in a ratio of 8:2 as the eluent.

Melting point: 99–104° C.

Analysis for $C_{25}H_{31}N_7O_3S$ (509.635)

Calculated: C 58.91%, H 6.13%, N 19.24%, S 6.29%;

Found: C 57.51%, H 6.25%, N 19.49%, S 6.22%.

EXAMPLE 35

2-[2-/4-(3-Trifluoromethylbenzyl)-1-piperazinyl/-ethyl-thio]-4,6-diamino-5-(4-methoxybenzyl)pyrimidine Solvent employed in the reaction: methanol.

Reaction time: 3 hours. The reaction mixture is worked up by method "A".

Yield: 17.8 g (67%).

Purification: recrystallization from aqueous ethanol.

Melting point: 164–165° C.

Analysis for $C_{26}H_{31}F_3N_6OS$ (532.636)

Calculated: C 58.63%, H .5.87%, N 15.78%, S 6.02%;

Found: C 58.16%, H 5.76%, N 15.28%, S 5.93%.

EXAMPLE 36

2-[2-/4-(3-Trifluoromethylbenzyl)-1-piperazinyl/ethylthio]-4,6-diamino-5-(2-methoxybenzyl)pyrimidine Solvent employed in the reaction: methanol.

Reaction time: 3 hours. The reaction mixture is worked up by method "A".

Yield: 14.7 g (55%).

Purification: recrystallization from aqueous ethanol.

Melting point: 140–144° C.

Analysis for $C_{26}H_{31}F_3N_6OS$ (532.636)

Calculated: C 58.63%, H 5.87%, N 15.78%, S 6.02%;

Found: C 56.51%, H 5.88%, N 15.47%, S 5.81%.

EXAMPLE 37

2-[2-/4-(2,6-Dinitro-4-trifluoromethyl-phenyl)-1-piperazinyl/ethylthio]-4,6-diamino-5-(4-methoxybenzyl)pyrimidine Solvent employed in the reaction: methanol.

Reaction time: 3 hours. The reaction mixture is worked up by method "B".

Yield: 13.4 g (44%).

Purification: recrystallization from aqueous ethanol.

Melting point: 178–180° C.

Analysis for $C_{25}H_{27}F_3N_8O_5S$ (608.604)

Calculated: C 49.34%, H 4.47%, N 18.41%, S 5.27%;

Found: C 48.69%, H 4.29%, N 18.35%, S 5.48%.

EXAMPLE 38

2-/2-(4-Benzyl-1-piperazinyl)ethylthio/-4,6-diamino-5-(4-chlorobenzyl)pyrimidine Solvent employed in the reaction: methanol.

Reaction time: 3 hours. The reaction mixture is worked up by method "B".

Yield: 14.1 g (60%).

Melting point: 182–184° C.

Analysis for $C_{24}H_{29}ClN_6S$ (469.056)

Calculated: C 61.46%, H 6.23%, Cl 7.56%, N 17.92%, S 6.84%;

Found: C 59.31%, H 6.25%, Cl 7.40%, N 17.58%, S 6.63%.

EXAMPLE 39

2-[2-/4-(2-Methylbenzyl)-1-piperazinyl/-ethylthio]-4,6-diamino-5-(2-chloro-benzyl)pyrimidine Solvent employed in the reaction: methanol.

Reaction time: 3 hours. The reaction mixture is worked up by method "A".

Yield: 22.5 g (93%).

Purification: recrystallization from aqueous ethanol.

Melting point: 146–148° C.

Analysis for $C_{25}H_{31}ClN_6S$ (483.083)

Calculated: C 62.16%, H 6.46%, Cl 7.34%, N 17.40%, S 6.64%;

Found: C 62.06%, H 6.47%, Cl 7.35%, N 17.30%, S 6.75%.

EXAMPLE 40

2-[2-/4-(4-Methylbenzyl)-1-piperazinyl/-ethylthio]-4,6-diamino-5-(2-chlorobenzyl)-pyrimidine Solvent employed in the reaction: methanol.
Reaction time: 3 hours. The reaction mixture is worked up by method "A".
Yield: 19.3 g (80%).
Purification: flash chromatography using a mixture of chloroform and methanol in a ratio of 95:5 as the eluent or recrystallization from aqueous ethanol.
Melting point: 166–168° C.
Analysis for $C_{25}H_{31}ClN_6S$ (483.083)
Calculated: C 62.16%, H 6.46%, Cl 7.34%, N 17.40%, S 6.64%;
Found: C 62.55%, H 6.56%, Cl 7.67%, N 16.86%, S 6.46%.

EXAMPLE 41
2-/2-(4-Benzyl-1-piperazinyl)ethylthio/-4-(2-chlorophenyl)-5-cyano-6-aminopyrimidine
Solvent employed in the reaction: dimethylformamide.
Reaction time: 30 hours. The reaction mixture is worked up by method "B".
Yield: 5.9 g (25%).
Purification: recrystallization from ethanol.
Melting point: 177–178° C.
Analysis for $C_{24}H_{25}ClN_6S$ (465.017)
Calculated: C 61.99%, H 5.42%, Cl 7.62%, N 18.07%, S 6.89%;
Found: C 61.45%, H 5.50%, Cl 7.54%, N 17.90%, S 6.69%.

EXAMPLE 42
2-[2-/4-(2-Cyanobenzyl)-1-piperazinyl/-ethylthio]-4,6-diamino-5-(2-chlorobenzyl)-pyrimidine
Solvent employed in the reaction: methanol.
Reaction time: 3 hours. The reaction mixture is worked up by method "A".
Yield: 22.2 g (90%).
Purification: recrystallization from aqueous ethanol.
Melting point: 170–173° C.
Analysis for $C_{25}H_{28}ClN_7S$ (494.066)
Calculated: C 60.78%, H 5.71%, Cl 7.18%, N 19.84%, S 6.49%;
Found: C 61.11%, H 5.86%, Cl 7.04%, N 19.09%, S 6.56%.

EXAMPLE 43
2-[2-/4-(4-Methoxybenzyl)-1-piperazinyl/-ethylthio]-4,6-diamino-5-(chlorobenzyl)-pyrimidine
Solvent employed in the reaction: methanol.
Reaction time: 3 hours. The reaction mixture is worked up by method "A".
Yield: 22.2 g (89%).
Purification: recrystallization from aqueous ethanol.
Melting point: 181–184° C.
Analysis for $C_{25}H_{31}ClN_6OS$ (499.082)
Calculated: C 60.17%, H 6.26%, Cl 7.10%, N 16.84%, S 6.42%;
Found: C 58.89%, H 6.07%, Cl 6.80%, N 16.15%, S 6.49%.

EXAMPLE 44
2-[2-/4-(3-Methoxybenzyl)-1-piperazinyl/-ethylthio]-4,6-diamino-5-(2-chlorobenzyl)-pyrimidine
Solvent employed in the reaction: methanol.
Reaction time: 3 hours. The reaction mixture is worked up by method "A".
Yield: 22.2 g (89%).
Purification: recrystallization from aqueous ethanol.
Melting point: 151–153° C.
Analysis for $C_{25}H_{31}ClN_6OS$ (499.082)
Calculated: C 60.17%, H 6.26%, Cl 7.10%, N 16.84%, S 6.42%;
Found: C 60.57%, H 6.16%, Cl 7.02%, N 16.64%, S 6.46%.

EXAMPLE 45
2-[2-/4-(2-Chlorobenzyl)-1-piperazinyl/ethylthio]-4,6-diamino-5-(2-chlorobenzyl)-pyrimidine
Solvent employed in the reaction: methanol.
Reaction time: 3 hours. The reaction mixture is worked up by method "B".
Yield: 10.8 g (43%).
Purification: recrystallization from aqueous ethanol.
Melting point: 178–183° C.
Analysis for $C_{24}H_{28}Cl_2N_6S$ (503.501)
Calculated: C 57.25%, H 5.61%, Cl 14.08%, N 16.69%, S 6.37%;
Found: C 57.45%, H 5.36%, Cl 13.59%, N 16.80%, S 6.14%.

EXAMPLE 46
2-[2-/4-(4-Chlorobenzyl)-1-piperazinyl/-ethylthio]-4,6-diamino-5-(2-chlorobenzyl)-pyrimidine
Solvent employed in the reaction: methanol.
Reaction time: 3 hours. The reaction mixture is worked up by method "A".
Yield: 10.82 g (43%).
Purification: recrystallization from aqueous ethanol.
Melting point: 173–175° C.
Analysis for $C_{24}H_{28}Cl_2N_6S$ (503.501)
Calculated: C 57.25%, H 5.61%, Cl 14.08%, N 16.69%, S 6.37%;
Found: C 56.48%, H 5.53%, Cl 13.59%, N 16.38%, S 6.11%.

EXAMPLE 47
2-[2-/4-(2-Chlorobenzyl)-1-piperazinyl/ethylthio]-4,6-diamino-5-(4-chlorobenzyl)-pyrimidine
Solvent employed in the reaction: methanol.
Reaction time: 24 hours. The reaction mixture is worked up by method "B".
Yield: 15.1 g (60%).
Purification: recrystallization from aqueous ethanol.
Melting point: 190–191° C.
Analysis for $C_{24}H_{28}Cl_2N_6S$ (503.501)
Calculated: C 57.25%, H 5.61%, Cl 14.08%, N 16.69%, S 6.37%;
Found: C 56.42%, H 5.67%, Cl 14.14%, N 16.25%, S 6.27%.

EXAMPLE 48
2-[2-/4-(4-Nitrobenzyl)-1-piperazinyl/-ethylthio]-4,6-diamino-5-(4-chlorobenzyl)-pyrimidine
Solvent employed in the reaction: methanol.
Reaction time: 3 hours. The reaction mixture is worked up by method "B".
Yield: 25.4 g (99%).
Purification: recrystallization from aqueous acetone.
Melting point: 133–135° C.
Analysis for $C_{24}H_{28}ClN_7O_2S$ (514.053)
Calculated: C 56.08%, H 5.49%, Cl 6.90%, N 19.07%, S 6.24%;
Found: C 56.55%, H 5.58%, Cl 6.76%, N 18.77%, S 6.15%.

EXAMPLE 49
2-[2-/4-(4-Nitrobenzyl)-1-piperazinyl/-ethylthio]-4,6-diamino-5-(2-chlorobenzyl)-pyrimidine Solvent employed in the reaction: methanol.
Reaction time: 3 hours. The reaction mixture is worked up by method "B".
Yield: 12.1 g (47%).
Purification: recrystallization from aqueous ethanol.
Melting point: 201–203° C.
Analysis for $C_{24}H_{28}ClN_7O_2S$ (514.053)
Calculated: C 56.08%, H 5.49%, Cl 6.90%, N 19.07 A, S 6.24%;
Found: C 56.05%, H 5.57%, Cl 6.69%, N 18.96%, S 6.17%.

EXAMPLE 50

2-[2-/4-(3-Trifluoromethylbenzyl)-1-piperazinyl/ethylthio]-4,6-diamino-5-(2-chlorobenzyl)pyrimidine
Solvent employed in the reaction: methanol.
Reaction time: 3 hours. The reaction mixture is worked up by method "A".
Yield: 15.3 g (57%).
Purification: recrystallization from aqueous ethanol.
Melting point: 121–123° C.
Analysis for $C_{25}H_{28}ClF_3N_6S$ (537.054)
Calculated: C 55.81%, H 5.43%, Cl 6.59%, N 15.62%, S 5.96%;
Found: C 53.98%, H 5.65%, Cl 6.47%, N 15.31%, S 5.79%.

EXAMPLE 51

2-/2-(4-Benzyl-1-piperazinyl)ethylthio/-4,6-diamino-5-(4-isopropylbenzyl)pyrimidine
Solvent employed in the reaction: methanol.
Reaction time: 7 hours. The reaction mixture is worked up by method "B".
Yield: 14.5 g (61%).
Purification: recrystallization from aqueous ethanol.
Melting point: 154–155° C.
Analysis for $C_{27}H_{36}N_6S$ (476.692)
Calculated: C 68.03%, H 7.61%, N 17.63%, S 6.73%;
Found: C 66.63%, H 7.57%, N 17.14%, S 6.96%.

EXAMPLE 52

2-[2-/4-(4-Nitrobenzyl)-1-piperazinyl/-ethylthio]-4,6-diamino-5-(4-isopropylbenzyl)-pyrimidine
Solvent employed in the reaction: methanol.
Reaction time: 3 hours. The reaction mixture is worked up by method "B".
Yield: 20.8 g (80%).
Purification: flash chromatography using a mixture of chloroform and acetone in a ratio of 2:8 as the eluent.
Melting point: 175–176° C.
Analysis for $C_{27}H_{35}N_7O_2S$ (521.690)
Calculated: C 62.16%, H 6.76%, N 18.79%, S 6.15%;
Found: C 62.38%, H 6.87%, N 18.40%, S 6.06%.

EXAMPLE 53

2-[2-/4-(2-Fluorobenzyl)-1-piperazinyl/-ethylthio]-4,6-diamino-5-(4-dimethylamino-benzyl)pyrimidine
Solvent employed in the reaction: methanol.
Reaction time: 3 hours. The reaction mixture is worked up by method "A".
Yield: 15.12 g (61%).
Purification: recrystallization from aqueous ethanol.
Melting point: 182–184° C.
Analysis for $C_{26}H_{34}FN_7S$ (495.670)
Calculated: C 63.00%, H 6.91%, N 19.78%, S 6.47%;
Found: C 62.86%, H 7.23%, N 19.73%, S 6.52%.

EXAMPLE 54

2-[2-/4-(2-Cyanobenzyl)-1-piperazinyl/-ethylthio]-4,6-diamino-5-(4-dimethylamino-benzyl)pyrimidine
Solvent employed in the reaction: methanol.
Reaction time: 3 hours. The reaction mixture is worked up by method "B".
Yield: 23.1 g (92%).
Purification: recrystallization from aqueous ethanol.
Melting point: 170–173° C.
Analysis for $C_{27}H_{34}N_8S$ (502.690)
Calculated: C 64.51%, H 6.82%, N 22.29%, S 6.38%;
Found: C 64.25%, H 6.95%, N 21.78%, S 6.12%.

EXAMPLE 55

2-[2-/4-(4-Methoxybenzyl)-1-piperazinyl/-ethylthio]-4,6-diamino-5-(4-dimethylamino-benzyl)pyrimidine
Solvent employed in the reaction: methanol.
Reaction time: 3 hours. The reaction mixture is worked up by method "A".
Yield: 21.8 g (86%).
Purification: recrystallization from aqueous ethanol.
Melting point: 192–195° C.
Analysis for $C_{27}H_{37}N_7OS$ (507.706)
Calculated: C 63.88%, H 7.35%, N 19.31%, S 6.31%;
Found: C 63.93%, H 7.13%, N 19.12%, S 6.51%.

EXAMPLE 56

2-[2-/4-(3-Chlorobenzyl)-1-piperazinyl/-ethylthio]-4,6-diamino-5-(4-dimethylamino-benzyl)pyrimidine
Solvent employed in the reaction: methanol.
Reaction time: 3 hours. The reaction mixture is worked up by method "A".
Yield: 16.60 g (65%).
Purification: recrystallization from aqueous ethanol.
Melting point: 179–182° C.
Analysis for $C_{26}H_{34}ClN_7S$ (512.125)
Calculated: C 60.98%, H 6.69%, Cl 6.92%, N 19.15%, S 6.26%;
Found: C 60.81%, H 6.56%, Cl 6.85%, N 19.00%, S 6.38%.

EXAMPLE 57

2-[2-/4-(4-Nitrobenzyl)-1-piperazinyl/-ethylthio]-4,6-diamiiino-5-(4-dimethylamino-benzyl)pyrimidine
Solvent employed in the reaction: methanol.
Reaction time: 3 hours. The reaction mixture is worked up by method "B".
Yield: 11 g (42%).
Purification: recrystallization from aqueous dimethylformamide.
Melting point: 219–220° C.
Analysis for $C_{26}H_{34}N_8O_2S$ (522.677)
Calculated: C 59.75%, H 6.56%, N 21.44%, S 6.13%;
Found: C 58.03%, H 6.32%, N 21.08%, S 5.94%.

EXAMPLE 58

2-[2-/4-(3-Trifluoromethylbenzyl)-1-piperazinyl/ethylthio]-4,6-diamino-5-(4-dimethylaminobenzyl)pyrimidine
Solvent employed in the reaction: methanol.
Reaction time: 3 hours. The reaction mixture is worked up by method "B".
Yield: 11.50 g (42%).
Purification: recrystallization from aqueous ethanol.
Melting point: 185–189° C.
Analysis for $C_{27}H_{34}F_3N_7S$ (545.678)
Calculated: C 59.32%, H 6.45%, N 17.94%, S 5.86%;
Found: C 58.44%, H 6.35%, N 18.01%, S 5.79%.

EXAMPLE 59

2-[2-/4-(4-Chlorobenzyl)-1-piperazinyl/-ethylthio]-4,6-diamino-5-(2-chloro-6-fluoro-benzyl)pyrimidine Solvent employed in the reaction: methanol.
Reaction time: 3 hours. The reaction mixture is worked up by method "B".
Yield: 11.7 g (45%).
Purification: recrystallization from aqueous ethanol.
Melting point: 202–206° C.
Analysis for $C_{24}H_{27}Cl_2FN_6S$ (521.491)
Calculated: C 55.28%, H 5.22%, Cl 13.60%, N 16.12%, S 6.15%;
Found: C 54.78%, H 5.20%, Cl 13.40%, N 16.22%, S 6.30%.

EXAMPLE 60
2-[2-/4-(4-Nitrobenzyl)-1-piperazinyl/-ethylthio]-4,6-diamino-5-(2-chloro-6-fluoro-benzyl)pyrimidine
Solvent employed in the reaction: methanol.
Reaction time: 3 hours. The reaction mixture is worked up by method "B".
Yield: 17.8 g (48%).
Purification: recrystallization from acetone.
Melting point: 202–204° C.
Analysis for $C_{24}H_{27}ClFN_7O_2S$ (532.044)
Calculated: C 54.18%, H 5.12%, Cl 6.66%, N 18.43%, S 6.03%;
Found: C 53.97%, H 5.04%, Cl 6.61%, N 17.73%, S 6.05%.

EXAMPLE 61
2-[2-/4-(2,6-Dinitro-4-trifluoromethyl-phenyl)-1-piperazinyl/ethylthio]-4,6-diamino-5-(2-chloro-6-fluorobenzyl)pyrimidine
Solvent employed in the reaction: methanol.
Reaction time: 3 hours. The reaction mixture is worked up by method "B".
Yield: 15.8 g (50%).
Purification: recrystallization from aqueous ethanol.
Melting point: 185–192° C.
Analysis for $C_{24}H_{23}ClF_4N_8O_4S$ (631.013)
Calculated: C 45.68%, H 3.67%, Cl 5.62%, N 17.76%, S 5.08%;
Found: C 45.56%, H 3.62%, Cl 5.49%, N 17.14%, S 5.25%.

EXAMPLE 62
2-[2-/4-(4-Nitrobenzyl)-1-piperazinyl/-ethylthio]-4,6-diamino-5-(4-trifluoromethyl-benzyl)pyrimidine
Solvent employed in the reaction: methanol.
Reaction time: 3 hours. The reaction mixture is worked up by method "B".
Yield: 12.6 g (46%).
Purification: recrystallization from aqueous dimethylformamide.
Melting point: 164–166° C.
Analysis for $C_{25}H_{28}F_3N_7O_2S$ (547.607)
Calculated: C 54.83%, H 5.15%, N 17.90%, S 5.86%;
Found: C 54.00%, H 5.18%, N 17.50%, S 6.06%.

EXAMPLE 63
2-[2-/4-(3-Trifluoromethylbenzyl)-1-piperazinyl/ethylthio]-4,6-diamino-5-(4-trifluoromethylbenzyl)pyrimidine
Solvent employed in the reaction: methanol.
Reaction time: 3 hours. The reaction mixture is worked up by method "A".
Yield: 14 g (49%).
Purification: flash chromatography using a mixture of chloroform and methanol in a ratio of 9:1 as the eluent.
Melting point: 127–129° C.
Analysis for $C_{26}H_{28}F_6N_6S$ (570.608)
Calculated: C 54.73%, H 4.95%, N 14.73%, S 5.62%;
Found: C 54.79%, H 4.80%, N 14.46%, S 5.74%.

EXAMPLE 64
2-[2-/4-(4-Nitrobenzyl)-1-piperazinyl/-ethylthio]-4,6-diamino-5-(4-bromo-benzyl)pyrimidine
Solvent employed in the reaction: methanol.
Reaction time: 3 hours. The reaction mixture is worked up by method "B".
Yield: 12.9 g (46%).
Purification: recrystallization from aqueous acetone.
Melting point: 169–173° C.
Analysis for $C_{24}H_{28}BrN_7O_2S$ (558.509)
Calculated: C 51.61%, H 5.05%, Br 14.31%, N 17.56%, S 5.74%;
Found: C 51.45%, H 5.04%, Br 13.94%, N 17.44%, S 5.50%.

EXAMPLE 65
2-[2-/4-(3-Methoxybenzyl)-1-piperazinyl/-ethylthio]-4,6-diamino-5-(3,4,5-trimethoxy-benzyl)pyrimidine
Solvent employed in the reaction: methanol.
Reaction time: 3 hours. The reaction mixture is worked up by method "A".
Yield: 17.2 g (62%).
Purification: recrystallization from aqueous ethanol.
Melting point: 137–138° C.
Analysis for $C_{28}H_{38}N_6O_4S$ (554.717)
Calculated: C 60.63%, H 6.91%, N 15.15%, S 5.78%;
Found: C 58.32%, H 7.05%, N 14.95%, S 5.62%.

EXAMPLE 66
2-[2-/4-(4-Methoxybenzyl)-1-piperazinyl/-ethylthio]-4,6-diamino-5-(3,4,5-trimethoxy-benzyl)pyrimidine
Solvent employed in the reaction: methanol.
Reaction time: 3 hours. The reaction mixture is worked up by method "A".
Yield: 23.6 g (85%).
Purification: flash chromatography using a mixture of chloroform and methanol in a ratio of 9:1 as the eluent.
Melting point: 152–154° C.
Analysis for $C_{28}H_{38}N_6O_4S$ (554.717)
Calculated: C 60.63%, H 6.90%, N 15.15%, S 5.78%;
Found: C 61.99%, H 6.89%, N 14.45%, S 5.52%.

EXAMPLE 67
2-[2-/4-(2-Chlorobenzyl)-1-piperazinyl/-ethylthio]-4,6-diamino-5-(3,4,5-trimethoxy-benzyl)pyrimidine
Solvent employed in the reaction: methanol. Reaction-time: 3 hours. The reaction mixture is worked up by method "A".
Yield: 22.4 g (80%).
Purification: recrystallization from aqueous ethanol.
Melting point: 170–172° C.
Analysis for $C_{27}H_{35}ClN_6O_3S$ (559.135)
Calculated: C 58.00%, H 6.31%, Cl 6.34%, N 15.03%, S 5.73;
Found: C 57.30%, H 6.30%, Cl 6.27%, N 14.80%, S 5.74%.

EXAMPLE 68
2-[2-/4-(4-Nitrobenzyl)-1-piperazinyl/-ethylthio]-4,6-diamino-5-(3,4,5-trimethoxy-benzyl)pyrimidine
Solvent employed in the reaction: methanol.
Reaction time: 3 hours. The reaction mixture is worked up by method "A".
Yield: 11.7 g (41%).
Purification: recrystallization from aqueous ethanol.

Melting point: 130–132° C.
Analysis for $C_{27}H_{35}N_7O_5S$ (569.688)
Calculated: C 56.93%, H 6.19%, N 17.21%, S 5.63%;
Found: C 56.67%, H 6.22%, N 17.38%, S 5.54%.

EXAMPLE 69

2-[2-/4-(3-Trifluoromethylbenzyl)-1-piperazinyl/ethylthio]-4,6-diamino-5-(3,4,5-trimethoxybenzyl)pyrimidine
Solvent employed in the reaction: methanol.
Reaction time: 3 hours. The reaction mixture is worked up by method "A".
Yield: 13 g (44%).
Purification: recrystallization from aqueous ethanol.
Melting point: 159–162° C.
Analysis for $C_{28}H_{35}F_3N_6O_3S$ (592.689)
Calculated: C 56.74%, H 5.95%, N 14.18%, S 5.41%;
Found: C 56.90%, H 6.04%, N 14.06%, S 5.62%.

EXAMPLE 70

2-[2-/4-(4-Nitrobenzyl)-1-piperazinyl/-ethylthio]-4,6-diamino-5-(4-benzyloxy-3-methoxybenzyl)pyrimidine
Solvent employed in the reaction: methanol.
Reaction time: 3 hours. The reaction mixture is worked up by method "B".
Yield: 14.5 g (47%).
Purification: recrystallization from aqueous ethanol.
Melting point: 171–173° C.
Analysis for $C_{32}H_{37}N_7O_4S$ (615.760)
Calculated: C 62.42%, H 6.06%, N 15.92%, S 5.21%;
Found: C 61.23%, H 5.83%, N 15.85%, S 5.22%.

EXAMPLE 71

2-[2-/4-(2-Nitro-4-trifluoromethylphenyl)-1-piperazinyl/ethylthio]-4,6-diamino-5-(4-methoxybenzyl)pyrimidine
Solvent employed in the reaction: methanol.
Reaction time: 2.5 hours. The reaction mixture is worked up by method "B".
Yield: 23.1 g (82%).
Melting point: 181–182° C.
Analysis for $C_{25}H_{28}F_3N_7O_3S$ (563.607)
Calculated: C 53.28%, H 5.01%, N 17.40%, S 5.69%;
Found: C 52.65%, H 4.89%, N 17.05%, S 5.91%.

EXAMPLE 72

2-[2-/4-(2-Chlorobenzyl)-1-piperazinyl/-ethylthio]-4,6-diamino-5-(4-methoxy-benzyl)pyrimidine
Solvent employed in the reaction: methanol.
Reaction time: 4 hours. The reaction mixture is worked up by method "B".
Yield: 16.0 g (64%).
Purification: recrystallization from aqueous ethanol.
Melting point: 173° C.
Analysis for $C_{25}H_{31}ClN_6OS$ (499.075)
Calculated: C 60.17%, H 6.26%, Cl 7.10%, N 16.84%, S 6.42%;
Found: C 59.95%, H 6.22%, Cl 6.99%, N 16.55%, S 6.50%.

EXAMPLE 73

2-[2-/4-(2-Chlorobenzyl)-1-piperazinyl/-ethylthio]-4,6-diamino-5-(4-benzyloxy-3-methoxybenzyl)pyrimidine
Solvent employed in the reaction: methanol.
Reaction time: 82 hours. The reaction mixture is worked up by method "B".
Yield: 25.7 g (85%).
Purification: recrystallization from benzene.
Melting point: 158–160° C.
Analysis for $C_{32}H_{37}ClN_6O_2S$ (605.201)
Calculated: C 63.51%, H 6.16%, Cl 5.86%, N 13.89%, S 5.30%;
Found: C 63.16%, H 6.12%, Cl 5.84%, N 13.84%, S 5.33%.

EXAMPLE 74

2-[2-/4-(2-Chlorobenzyl)-1-piperazinyl/-ethylthio]-4,6-diamino-5-(4-isopropyl-benzyl)pyrimidine
Solvent employed in the reaction: methanol.
Reaction time: 3 hours. The reaction mixture is worked up by method "B".
Yield: 16.1 g (63%).
Purification: recrystallization from ethanol.
Melting point: 138–140° C.
Analysis for $C_{27}H_{35}ClN_6S$ (511.130)
Calculated: C 63.45%, H 6.90%, Cl 6.94%, N 16.44%, S 6.27%;
Found: C 63.32%, H 7.00%, Cl 6.76%, N 16.34%, S 6.30%.

EXAMPLE 75

2-/2-(4-Benzyl-1-piperazinyl)ethylthio/-4,6-diamino-5-(4-benzyloxy-3-methoxybenzyl)-pyrimidine
Solvent employed in the reaction: ethanol.
Reaction time: 7.5 hours. The reaction mixture is worked up by method "C".
Yield: 26.6 g (93%).
Purification: recrystallization from methanol.
Melting point: 166–167° C.
Analysis for $C_{32}H_{38}N_6O_2S$ (570.759)
Calculated: C 67.34%, H 6.71%, N 14.72%, S 5.62%;
Found: C 66.52%, H 6.68%, N 14.36%, S 5.55%.

EXAMPLE 76

2-[2-/4-(2,6-Dinitro-4-trifluoromethyl-phenyl)-1-piperazinyl/ethylthio]-4-methyl-5-(2-hydroxyethyl)uracil
Solvent employed in the reaction: methanol.
Reaction time: 1.5 hours. The reaction mixture is worked up by method "B".
Yield: 13.8 g (52%).
Purification: stirring in ethyl acetate.
Melting point: 196–197° C.
Analysis for $C_{20}H_{23}F_3N_6O_6S$ (532.502)
Calculated: C 45.11%, H 4.35%, N 15.78%, S 6.02%;
Found: C 46.30%, H 4.35%, N 15.55%, S 6.29%.

EXAMPLE 77

2-[2-/4-(2-Nitro-4-trifluoromethylphenyl)-1-piperazinyl/-ethylthio]-4-methyl-5-(2-hydroxyethyl)uracil
Solvent employed in the reaction: ethanol.
Reaction time: 1 hour. The reaction mixture is worked up by method "A".
Yield: 17.6 g (72%).
Purification: stirring in hexane.
Melting point: 133–135° C.
Analysis for $C_{20}H_{24}F_3N_5O_4S$ (487.506)
Calculated: C 49.28%, H 4.96%, N 14.37%, S 6.58%;
Found: C 48.05%, H 4.75%, N 14.38%, S 6.56%.

EXAMPLE 78

2-[2-/4-(2,6-Dinitro-4-trifluoromethyl-phenyl)-1-piperazinyl/ethylthio]-4-methyl-uracil
Solvent employed in the reaction: methanol.
Reaction time: 3 hours. The reaction mixture is worked up by method "B".
Yield: 11 g (45%).
Purification: recrystallization from ethanol.
Melting point: 226–228° C.

Analysis for $C_{18}H_{19}F_3N_6O_5S$ 488.45
Calculated: C 44.26%, H 3.92%, F 11.67%, N 17.21%, S 6.56%;
Found: C 44.04%, H 4.07%, F 12.07%, N 16.76%, S 6.56%.

EXAMPLE 79

2-[2-/4-(2,6-Dinitro-4-trifluoromethyl-phenyl)-1-piperazinyl/ethylthio]-4-amino-uracil Solvent employed in the reaction: methanol.
Reaction time: 3 hours. The reaction mixture is worked up by method "B".
Yield: 17.6 g (72%).
Purification: flash chromatography using a mexture of chloroform and methanol in a ratio of 9:1 as the eluent, then recrystallization from aqueous ethanol.
Melting point: 257–259° C.
Analysis for $C_{17}H_{18}F_3N_7OS$ (489.44)
Calculated: C 41.72%, H 3.71%, F 11.65%, N 20.03%, S 6.55%;
Found: C 42.10%, H 3.64%, F 11.66%, N 20.23%, S 6.66%.

EXAMPLE 80

2-[2-/4-(2-Nitro-4-trifluoromethylphenyl)-1-piperazinyl/ethylthio]-4-(4-methoxy-phenyl)-5-cyano-6-amino-3,4-dihydropyrimidine Solvent employed in the reaction: methanol.
Reaction time: 1 hour. The reaction mixture is worked up by method "B".
Yield: 20.6 g (73.4%).
Melting point: 225–226° C.
Analysis for $C_{25}H_{26}F_3N_7O_3S$ (561.591)
Calculated: C 53.47%, H 4.67%, N 17.46%, S 5.71%;
Found: C 53.54%, H 4.69%, N 17.18%, S 5.89%.

EXAMPLE 81

2-[2-/4-(2-Nitro-4-trifluoromethylphenyl)-1-piperazinyl/ethylthio]-4-(2-methoxy-phenyl)-5-cyano-6-amino-3,4-dihydropyrimidine Solvent employed in the reaction: methanol.
Reaction time: 1 hour. The reaction mixture is worked up by method "B".
Yield: 24.8 g (88%).
Melting point: 213–215° C.
Analysis for $C_{25}H_{26}F_3N_7O_3S$ (561.591)
Calculated: C 53.47%, H 4.67%, N 17.46%, S 5.71%;
Found: C 53.67%, H 4.74%, N 17.27%, S 5.95%.

EXAMPLE 82

2-[2-/4-(2-Nitro-4-trifluoromethylphenyl)-1-piperazinyl/ethylthio]-4-(4-chlorophenyl)-5-cyano-6-amino-3,4-dihydropyrimidine Solvent employed in the reaction: ethanol.
Reaction time: 1 hour. The reaction mixture is worked up by method "B". Yield; 24.9 g (87.9%).
Melting point: 217–219° C.
Analysis for $C_{24}H_{23}ClF_3N_7O_2S$ (556.007)
Calculated: C 50.93%, H 4.10%, Cl 6.26%, N 17.32%, S 5.66%;
Found: C 50.09%, H 4.02%, Cl 6.32%, N 16.51%, S 5.65%.

EXAMPLE 83

2-[2-/4-(2-Nitro-4-trifluoromethylphenyl)-1-piperazinyl/ethylthio]-4-(2-chlorophenyl)-5-cyano-6-amino-3,4-dihydropyrimidine Solvent employed in the reaction: ethanol.
Reaction time: 45 minutes. The reaction mixture is worked up by method "B".
Yield: 25.7 g (90.8%).
Melting point: 235–236° C.
Analysis for $C_{24}H_{23}ClF_3N_7O_2S$ (556.007)
Calculated: C 50.93%, H 4.10%, Cl 6.26%, N 17.32%, S 5.66%;
Found: C 50.55%, H 4.11%, Cl 6.19%, N 17.20%, S 5.72%.

EXAMPLE 84

2-[2-/4-(2-Nitro-4-trifluoromethylphenyl)-1-piperazinyl/ethylthio]-4-(4-dimethyl-aminophenyl)-5-cyano-6-amino-3,4-dihydro-pyrimidine Solvent employed in the reaction: methanol.
Reaction time: 1.5 hours. The reaction mixture is worked up by method "B".
Yield: 25.8 g (89.8%).
Purification: recrystallization from aqueous acetone.
Melting point: 221–223° C.
Analysis for $C_{26}H_{29}F_3N_8O_2S$ (574.634)
Calculated: C 54.35%, H 5.09 t; N 19.50%, S 5.58%;
Found: C 54.48%, H 5.11%, N 19.32%, S 5.72%.

EXAMPLE 85

2-[2-/4-(2-Nitro-4-trifluoromethylphenyl)-1-piperazinyl/ethylthio]-4-phenyl-5-cyano-6-amino-3,4-dihydropyrimidine Solvent employed in the reaction: ethanol.
Reaction time: 0.5 hours. The reaction mixture is worked up by method "B".
Yield: 24 g (90.3%).
Melting point: 240–242° C.
Analysis for $C_{24}H_{24}F_3N_7O_2S$ (531.565)
Calculated: C 54.23%, H 4.55%, N 18.44%, S 6.03%;
Found: C 53.63%, H 4.49%, N 18.08%, S 6.21%.

EXAMPLE 86

2-[2-/4-(2,6-Dinitro-4-trifluoromethyl-phenyl)-1-piperazinyl/ethylthio]-4-(4-methoxyphenyl)-5-cyano-6-aminopyrimidine Solvent employed in the reaction: methanol.
Reaction time: 20 minutes. The reaction mixture is worked up by method "C".
Yield: 15.7 g (51.7%).
Purification: recrystallization from a mixture of ethanol and acetone.
Melting point: 245–247° C.
Analysis for $C_{25}H_{23}F_3N_8O_5S$ (604.573)
Calculated: C 49.67%, H 3.83%, N 18.53%, S 5.30%;
Found: C 49.16%, H 4.05%, N 18.30%, S 5.38%.

EXAMPLE 87

2-[2-/4-(2-Nitro-4-trifluoromethylphenyl)-1-piperazinyl/ethylthio]-4-(4-bromophenyl-5-cyano-6-amino-3,4-dihydropyrimidine Solvent employed in the reaction: ethanol.
Reaction time: 1 hour. The reaction mixture is worked up by method "B".
Yield: 26.4 g (86.4%).
Melting point: 220–222° C.
Analysis for $C_{24}H_{23}BrF_3N_7O_2S$ (610.467)
Calculated: C 47.22%, 1 3.80%, Br 13.09%, N 16.06%, S 5.25%;
Found: C 46.50%, H 3.73%, Br 13.26%, N 15.99%, S 5.20%.

EXAMPLE 88

2-[2-/4-(2-Nitro-4-trifluoromethylphenyl)-1-piperazinyl/ethylthio]-4-(4-benzyloxy-3-methoxyphenyl-5-cyano-6-amino-3,4-dihydropyrimidine Solvent employed in the reaction: ethanol.
Reaction time: 1 hour. The reaction mixture is worked up by method "B".
Yield: 27.7 g (83.0%).
Purification: recrystallization from ethyl acetate.
Melting point: 162–164° C.
Analysis for $C_{32}H_{32}F_3N_7O_4S$ (667.717)
Calculated: C 57.56%, H 4.83%, N 14.68%, S 4.80%;
Found: C 57.10%, H 4.76%, N 14.46%, S 4.99%.

EXAMPLE 89

2-[2-/4-(2-Nitro-4-trifluoromethylphenyl)-1-piperazinyl/ethylthio]-2–4-(3,4,5-trimethoxyphenyl)-5-cyano-6-amino-3,4-dihydropyrimidine Solvent employed in the reaction: ethanol.
Reaction time: 1 hour. The reaction mixture is worked up by method "B".
Yield: 26.2 g (84.4%).
Melting point: 204–206° C.
Analysis for $C_{27}H_{30}F_3N_7O_5S$ (621.644)
Calculated: C 52.17%, H 4.86%, N 15.77%, S 5.16%;
Found: C 52.16%, H 4.72%, N 15.98%, S 5.32%.

EXAMPLE 90

2-[2-/4-(2,6-Dinitro-4-trifluoromethyl-phenyl)piperazinyl/ethylthio]-4-(2-methoxy-phenyl)-5-cyano-6-aminopyrimidine Solvent employed in the reaction: methanol.
Reaction time: 3 hours. The reaction mixture is worked up by method "B".
Yield: 10.7 g (35.4%).
Purification: recrystallization from aqueous ethanol.
Melting point: 194–195° C.
Analysis for $C_{25}H_{23}F_3N_8O_5S$ (604.573)
Calculated: C 49.67%, H 3.83%, N 18.53%, S 5.30%;
Found: C 48.27%, H 3.85%, N 18.29%, S 5.26%.

EXAMPLE 91

2-[2-/4-(2-Nitro-4-trifluoromethylphenyl)-1-piperazinyl/ethylthio]-4-methyl-5-ethoxy-carbonyl-6-phenyl-3,4-dihydropyrimidine Solvent employed in the reaction: methanol.
Reaction time: 1.5 hours. The reaction mixture is worked up by method "A".
Yield: 12.2 g (42.1%).
Purification: recrystallization from a mixture of methanol and hexane.
Melting point: 110–112° C.
Analysis for $C_{27}H_3F_3N_5O_4S$ (577.632)
Calculated: C 56.14%, H 5.23%, N 12.12%, S 5.55%;
Found: C 54.41%, H 4.91%, N 12.24%, S 5.63%.

EXAMPLE 92

2-[2-/4-(2,6-Dinitro-4-trifluoromethyl-phenyl)-1-piperazinyl/ethylthio]-4-(4-chloro-phenyl)-5-cyano-6-aminopyrimidine Solvent employed in the reaction: ethanol.
Reaction time: 1 hour. The reaction mixture is worked up by method "B".
Yield: 15.2 g (50.9%).
Purification: recrystallization from ethyl acetate.
Melting point: 247–249° C.
Analysis for $C_{23}H_{20}C_1F_3N_8O_4S$ (596.977)
Calculated: C 46.28%, H 3.38%, Cl 5.94%, N 18.77%, S 5.37%;
Found: C 46.94%, El 3.27%, Cl 5.84%, N 18.37%, S 5.23%.

EXAMPLE 93

2-/2-(4-Benzyl-1-piperazinyl)ethylthio/-4-(4-methoxyphenyl)-5-cyano-6-aminopyrimidine Solvent employed in the reaction: methanol.
Reaction time: 3 hours. The reaction mixture is worked up by method "A".
Yield: 13.1 g (55.5%).
Melting point: 156–158° C.
Analysis for $C_{25}H_{30}N_6OS$ (462.617).
Calculated: C 64.91%, H 6.54%, N 18.17%, S 6.93%;
Found: C 64.87%, H 6.59%, N 17.86%, S 6.98%.

EXAMPLE 94

2-[2-14-(2,6-Dinitro-4-trifluoromethyl-phenyl)-1-piperazinyl/ethylthio]-4-(4-benzyloxy-3-methoxyphenyl)-5-cyano-6-aminopyrimidine Solvent employed in the reaction: ethanol.
Reaction time: 1 hour. The reaction mixture is worked up by method "B".
Yield: 25.0 g (70.2%).
Purification: recrystallization from ethyl acetate.
Melting point: 201–203° C.
Analysis for $C_{32}H_{29}F_3N_8O_6S$ (710.698)
Calculated: C 54.08%, H 4.11%, N 15.77%, S 4.51%;
Found: C 53.49%, H 3.99%, N 15.70%, S 4.38%.

EXAMPLE 95

2-/2-(4-Benzyl-1-piperazinyl)ethylthio/-4-(2-chlorophenyl)-5-cyano-6-amino-3,4-dihydropyrimidine Solvent employed in the reaction: methanol.
Reaction time: 14 hours. The reaction mixture is worked up by method "C".
Yield: 15.9 g (67.9%).
Melting point: 183–184° C.
Analysis for $C_{24}27ClN_6S$ (467.033)
Calculated: C 61.72%, H 5.83%, Cl 7.59%, N 17.99%, S 6.86%;
Found: C 62.20%, H 5.76%, Cl 7.85%, N 18.13%, S 7.04%.

EXAMPLE 96

2-/2-(4-Benzyl-1-piperazinyl)ethylthio/-4-phenyl-5-cyano-6-amino-3,4-dihydropyrimidine Solvent employed in the reaction: methanol.
Reaction time: 2.5 hours. The reaction mixture is worked up by method "B".
Yield: 11.9 g (55.1%).
Purification: recrystallization from ethanol.
Melting point: 175–176° C.
Analysis for $C_{24}H_{28}N_6S$ (432.591)
Calculated: C 66.64%, H 6.52%, N 19.43%, S 7.41%;
Found: C 66.54%, H 6.50%, N 19.28%, S 7.29%.

EXAMPLE 97

2-[2-/4-(2-Nitrobenzyl)-1-piperazinyl/-ethylthio]-4-phenyl-5-cyano-6-amino-3,4-dihydropyrimidine Solvent employed in the reaction: dimethylformamide.
Reaction time: 3 hours. The reaction mixture is worked up by method "C".
Yield: 13.8 g (57.6%).
Melting point: 198–199° C.
Analysis for $C_{24}H_{27}N_7O_2S$ (477.589)
Calculated: C 60.36%, H 5.70%, N 20.53%, S 6.71%;
Found: C 59.61%, H 5.53%, N 20.52%, S 6.63%.

EXAMPLE 98

2-[2-(4-(2-Nitro-4-trifluoromethylphenyl)-1-piperazinyl/ethylthio]-4-phenyl-5-cyano-6-aminopyrimidine Solvent employed in the reaction: dimethylformamide.
Reaction time: 10 hours. The reaction mixture is worked up by method "B".
Yield: 20.3 g (76.8%).
Purification: recrystallization from ethanol, then from benzene.
Melting point: 189–190° C.
Analysis for $C_{24}H_{22}F_3N_7O_2S$ (529.549)
Calculated: C 54.44%, H 4.19%, N 18.52%, S 6.05%;
Found: C 55.59%, H 4.33%, N 18.02%, S 5.92%.

EXAMPLE 99
2-[2-/4-(2-Nitro-4-trifluoromethylphenyl)-1-piperazinyl/ethylthio]-4-(2-methoxy-phenyl)-5-cyano-6-aminopyrimidine
Solvent employed in the reaction: dimethylformamide.
Reaction time: 35 hours. The reaction mixture is worked up by method "B".
Yield: 20.6 g (73.6%).
Purification: recrystallization from benzene, then the crystals are suspended in kerosene.
Melting point: 145–147° C.
Analysis for $C_{25}H_{24}F_3N_7O_3S$ (559.575)
Calculated: C 53.66%, H 4.32%, N 17.52%, S 5.73%;
Found: C 54.04%, H 4.36%, N 17.13%, S 5.94%.

EXAMPLE 100
2-[2-/4-(3-Trifluoromethylbenzyl)-1-piperazinyl/ethylthio]-4-(2-chlorophenyl)-5-cyano-6-aminopyrimidine
Solvent employed in the reaction: dimethylformamide.
Reaction time: 5 hours. The reaction mixture is worked up by method "A".
Yield: 16.7 g (63.5%).
Purification: recrystallization from ethanol.
Melting point: 166–167° C.
Analysis for $C_{25}H_{24}ClF_3N_6S$ (533.02)
Calculated: C 56.34%, H 4.54%, Cl 6.65%, N 15.77%, S 6.01%;
Found: C 55.78%, H 4.42%, Cl 6.68%, N 15.81%, S 6.20%.

EXAMPLE 101
2-[2-/4-(2-Chlorobenzyl)-1-piperazinyl/-ethylthio]-4,6-diamino-5-(4-dimethylamino-benzyl)pyrimidine
Solvent employed in the reaction: methanol.
Reaction time: 40 hours. The reaction mixture is worked up by method "A".
Yield: 5.85 g (22.9%).
Purification: recrystallization from aqueous acetone.
Melting point: 156.4–156.6° C.
Analysis for $C_{26}H_{34}ClN_7S$ (512.13)
Calculated: C 60.98%, H 6.69%, Cl 6.92%, N 19.15%, S 6.26%;
Found: C 60.80%, H 6.67%, Cl 6.83%, N 18.85%, S 6.11%.

EXAMPLE 102
2-[2-/4-(2-Chlorobenzyl)-1-piperazinyl/-ethylthio]-4,6-diamino-5-(4-dimethylamino-benzyl)pyrimidine
Solvent employed in the reaction: methanol.
Reaction time: 40 hours. The reaction mixture is worked up by method "A".
Yield: 5.30 g (26.5%).
Purification: recrystallization from aqueous acetone.
Melting point: 90–93° C.
Analysis for $C_{26}H_{34}ClN_7S$ (512.13)
Calculated: C 62.97%, H 8.05%, N 20.98%, S 8.00%;
Found: C 62.36%, H 7.92%, N 20.34%, S 7.86%.

EXAMPLE 103
2-/11-(4-Benzyl-1-piperazinyl)undecylthio/-4,6-diaminopyrimidine×MeOH
Solvent employed in the reaction: methanol.
Reaction time: 12 hours. The reaction mixture is worked up by method "A".
Yield: 18.50 g (78.0%).
Purification: recrystallization from aqueous ethanol.
Melting point: 109–111° C.
Analysis for $C_{27}H_{46}N_6OS$ (502.77)
Calculated: C 64.50%, H 9.22%, N 16.72%, S 6.38%;
Found: C 62.57%, H 8.90%, N 16.43%, S 6.36%.

EXAMPLE 104
2-[11-/4-(4-Nitrobenzyl)-1-homopiperazinyl/-1-undecylthio]-4,6-diamino-pyrimidine
Solvent employed in the reaction: methanol.
Reaction time: 12 hours. The reaction mixture is worked up by method "A".
Yield: 18.2 g (68.0%).
Purification: recrystallization from a mixture of chloroform and methanol.
Melting point: 185–187° C.
Analysis for $C_{27}H_{43}N_7O_2S$ (529.753)
Calculated: C 61.22%, H 8.18%, N 8.51%, S 6.05%,
Found: C 61.05%: H 8.10%, N 8.60%, S 6.09%.

Preparation of the acid addition salts The pharmaceutically acceptable acid addition salts of the compounds of the formula I are prepared according to the following general method:

0.05 moles of the compound of the formula I are dissolved in 1000 ml of ethanol, and, to the solution obtained, 250 ml of ethanol containing 25 per cent of hydrochlorid acid are added. The reaction mixture is stirred at reflux temperature for 2 hours, then the solvent is removed under reduced pressure. The solid residue is purified by suspending it in 100 ml of anhydrous ethanol, stirring the suspension for 20 minutes, then removing the solvent under reduced pressure. The purification procedures are repeated three times, and the product is dried in a drying oven until a constant weight is attained.

EXAMPLE 105
2-[2-/4-(2-Methylbenzyl)-1-piperazinyl/-ethylthio]-4,6-diamino-5-(2-chloro-benzyl)pyrimidine trihydrochloride
Yield: 27 g (91%).
Melting point: 179–186° C.
Analysis for $C_{25}H_{34}Cl_4N_6S$ (592.466)
Calculated: C 50.68%, H 5.78%, Cl 23.94%: N 14.18%: S 5.4.1%;
Found: C 49.75%. H 5.75%, Cl 23.46%, N 14.02%, S 5.45%.

EXAMPLE 106
2-[2-/4-(3-Methoxybenzyl)-1-piperazinyl/-ethylthio]-4,6-diamino-5-(3:4.5-trimethoxy-benzyl)pyrimidine trihydrochloride
Yield: 30 g (89%).
Melting point: 171–179° C.
Analysis for $C_{28}H_{41}Cl_3N_6O_4S$ (664.100)
Calculated: C 50.64%. 11 6.22%, Cl 16.02%, N 12.65%, S 4.83%;
Found: C 50.07%, H 6.52%, Cl 15.79%, N 12.20% S 4.64%.

EXAMPLE 107
2-[2-/4-(2-Cyanobenzyl)-1-piperazinyl/-ethylthio]-4,6-diamino-5-(4-methoxy-benzyl)pyrimidine trihydrochloride Yield: 28 g (92%). Meltnang point: 199–210° C.
Analysis for $C_{26}H_{34}Cl_3N_7OS$ (599.030)
Calculated: C 52.13%: H 5.72%, Cl 17.76%, N 16.37%, S 5.35%;
Found: C 51.76%, H 5.65%, Cl 17.57%, N 16.06%, S 5.45%.

EXAMPLE 108

2-[2-/4-(3-Methoxybenzyl)-1-piperazinyl/-ethylthio]-4,6-diamino-5-benzylpyrimidine trihydrochloride
Yield: 25 g (87%).
Melting point: 163–174° C.
Analysis for $C_{25}H_{35}Cl_3N_6OS$ (574.020)
Calculated: C 52.31%, H 6.15%: Cl 18.53%, N 14.64% S 5.59%;
Found: C 51.29%. H 6.17%, Cl 19.08%, N 14.26%, S 5.80%.

EXAMPLE 109

2-[2-/4-(3-Trifluoromethylbenzyl)-1-piperazinyl/ethylthio]-4,6-diamino-5-(3,4,5-trimethoxybenzyl)pyrimidine trihydrochloride
Yield: 30 g (85%).
Melting point: 162–165° C.
Analysis for $C_{28}H_{38}Cl_3F_3N_6O_3S$ (702.072)
Calculated: C 47.90%, H 5.46%, Cl 15.15%, N 11.97%: S 4.57%;
Found: C 45.84%, H 5.60%, Cl 14.51%, N 11.40%, S 4.63%.

EXAMPLE 110

2-/ 2-/4.-(3-Methoxybenzyl)-1-piperazinyl/-ethylthio/-4,6-diamino-5-(4-methoxy-benzyl)pyrimidine trihydrochloride
Yield: 26 g (86%).
Melting point: 172–182° C.
Analysis for $C_{26}H_{37}Cl_3N_6O_2S$ (604.047)
Calculated: C 51.70%, H 6.17%, Cl 17.61%, N 13.91%, S 5.31%;
Found: C 50.01%, H 6.27%, Cl 16.94%, N 13.29%, S 5.24%.

What is claimed is:
1. A compound of the formula (I)

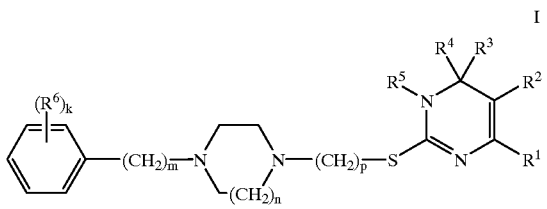

wherein
$R^1$ and $R^3$ represent an amino group,
$R^2$ stands for a hydrogen or a benzyl group optionally bearing 1 to 3 substituents selected from the group consisting of, independently, a fluoro, a chloro, a methoxy group and a dimethylamino group,
$R^4$ forms with $R^5$ a valence bond,
$R^6$ means a fluoro, a chloro, a nitro group, a cyano group, a methyl group, a methoxy group or a trifluoromethyl group,
k has a value of 1,
m has a value of 1,
n has a value of 1, and
p has a value of 2, or a pharmaceutically acceptable acid addition salt thereof.

2. 2-{2-(4-(4-(Nitrobenzyl)-1-piperazinyl)ethylthio}-4,6-diamino-5-benzylpyrimidine or a pharmaceutically acceptable acid addition salt thereof.

3. A pharmaceutical composition comprising a piperazinylalkylthiopyrimidine derivative of formula (I)

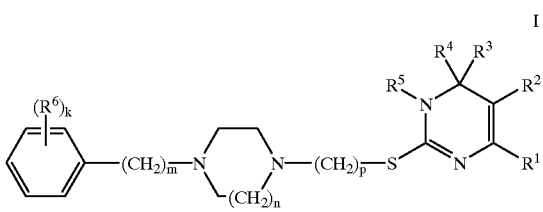

wherein
$R^1$ and $R^3$ represent an amino group,
$R^2$ stands for a hydrogen or a benzyl group optionally bearing 1 to 3 substituents selected from the group consisting of, independently, a fluoro, a chloro, a methoxy group and a dimethylamino group,
$R^4$ forms with $R^5$ a valence bond,
$R^6$ means a fluoro, a chloro, a nitro group, a cyano group, a methyl group, a methoxy group or a trifluoromethyl group,
k has a value of 1,
m has a value of 1,
n has a value of 1, and
p has a value of 2, or a pharmaceutically acceptable acid addition salt thereof as the active ingredient and one or more usual carrier(s).

4. A pharmaceutical composition comprising a piperazinylalkylthiopyrimidine derivative which is 2-{2-(4-(4-nitrobenzyl)-1-piperazinyl)ethylthio}4,6-diamino-5-benzylpyrimidine or a pharmaceutically acceptable acid addition salt thereof as the active ingredient and one or more usual carrier(s).

* * * * *